United States Patent
Ross et al.

(10) Patent No.: US 12,236,320 B2
(45) Date of Patent: Feb. 25, 2025

(54) PASSIVE HEIGHTENED NEED PREDICTION

(71) Applicant: Optum Services (Ireland) Limited, Dublin (IE)

(72) Inventors: Peter Joseph Ross, Dublin (IE); Damian Kelly, Kildare (IE)

(73) Assignee: Optum Services (Ireland) Limited, Dublin (IE)

( * ) Notice: Subject to any disclaimer, the term of this patent is extended or adjusted under 35 U.S.C. 154(b) by 296 days.

(21) Appl. No.: 16/866,844

(22) Filed: May 5, 2020

(65) Prior Publication Data

US 2021/0350271 A1 Nov. 11, 2021

(51) Int. Cl.
G06N 20/00 (2019.01)
G06F 18/214 (2023.01)
G06N 5/04 (2023.01)

(52) U.S. Cl.
CPC ........... *G06N 20/00* (2019.01); *G06F 18/214* (2023.01); *G06N 5/04* (2013.01)

(58) Field of Classification Search
CPC ......... G06N 20/00; G06N 5/04; G06K 9/6256
See application file for complete search history.

(56) References Cited

U.S. PATENT DOCUMENTS

| 9,849,281 | B2 | 12/2017 | Imran et al. | |
|---|---|---|---|---|
| 11,087,010 | B2 * | 8/2021 | Bender | G06F 21/6218 |
| 11,238,979 | B1 * | 2/2022 | Schilling | G16B 40/00 |
| 2014/0142965 | A1 | 5/2014 | Houston et al. | |
| 2018/0068080 | A1 | 3/2018 | Parate et al. | |
| 2018/0075219 | A1 * | 3/2018 | Klein | G16H 20/70 |
| 2019/0209022 | A1 * | 7/2019 | Sobol | A61B 5/02055 |
| 2019/0239564 | A1 | 8/2019 | Utley et al. | |
| 2019/0261855 | A1 | 8/2019 | Utley et al. | |
| 2019/0340906 | A1 * | 11/2019 | Williams | G08B 21/0277 |
| 2019/0373078 | A1 | 12/2019 | Klein et al. | |

(Continued)

FOREIGN PATENT DOCUMENTS

WO 1995/021419 A1 8/1995

OTHER PUBLICATIONS

"Health Effects of Cigarette Smoking," Centers for Disease Control and Prevention, (3 pages), (article, online), [retrieved from the Internet Aug. 3, 2020] <URL: https://www.cdc.gov/tobacco/data_statistics/fact_sheets/health_effects/effects_cig_smoking/>.

(Continued)

*Primary Examiner* — Courtney Harmon
(74) *Attorney, Agent, or Firm* — ALSTON & BIRD LLP

(57) ABSTRACT

There is a need for more effective and efficient heightened need prediction. In one example, a method comprises, during an online prediction phase: receiving incoming monitoring data associated with the user profile; performing anomaly reduction on the incoming monitoring data to generate anomaly-reduced incoming monitoring data; generating an incoming monitoring window based on the anomaly-reduced incoming monitoring data; processing the incoming monitoring window using a trained heightened need prediction machine learning model to determine a heightened need prediction for the incoming monitoring window; and in response to determining that the heightened need prediction is positive, performing one or more responsive actions by communicating with one or more client devices associated with the user profile.

20 Claims, 12 Drawing Sheets

(56) References Cited

U.S. PATENT DOCUMENTS

2021/0233654 A1* 7/2021 Arthur ............ G06Q 10/063114
2022/0076822 A1* 3/2022 Liu ........................ G06F 21/31

OTHER PUBLICATIONS

"Quitting Smoking Among Adults—United States, 2001-2010," Centers for Disease Control and Prevention, Nov. 11, 2011, vol. 60, No. 44, pp. 1513-1519, (article, online), [retrieved from the Internet Aug. 3, 2020] <URL: https://www.cdc.gov/mmwr/preview/mmwrhtml/mm6044a2.htm/>.

"Tobacco," World Health Organization, May 27, 2020, (8 pages), (article, online), [retrieved from the Internet Aug. 3, 2020] <URL: https://www.who.int/en/news-room/fact-sheets/detail/tobacco>.

Boyer, Edward W. et al. "Preliminary Efforts Directed Toward The Detection of Craving of Illicit Substances: The iHeal Project," Journal of Medical Toxicology, (2012), vol. 8, No. 1, pp. 5-9. DOI: 10.1007/x13181-011-0200-4.

Brendryen, Havar et al. "Looking Inside The Black Box: Using Intervention Mapping to Describe the Development of the Automated Smoking Cessation Intervention 'Happy Ending'," Journal of Smoking Cessation, (2010), vol. 5, No. 1, pp. 29-56. DOI: 10.1375jsc.5.1.29.

Chatterjee, Soujanya et al. "mCrave: Continuous Estimation of Craving During Smoking Cessation," InProceedings of the 2016 ACM International Joint Conference on Pervasive and Ubiquitous Computing, Sep. 12, 2016, pp. 863-874, Heidelberg, Germany. DOI: 10.1145/2971648.2971672.

Ertin, Emre et al. "AutoSense: Unobtrusively Wearable Sensor Suite for Inferring the Onset, Causality, and Consequences of Stress in the Field," InProceedings of the 9th ACM Conference on Embedded Networked Sensor Systems, Nov. 1, 2011, pp. 274-287.

Hughes, John R. et al. "Shape of the Relapse Curve and Long-Term Abstinence Among Untreated Smokers," Society for the Study of Addiction, (2004), vol. 99, No. 1, pp. 29-38.

Jaimes, Luis G. et al. "Trends in Mobile Cyber-Physical Systems for Health Just-In Time Interventions," Proceedings of the IEEE SoutheastCon 2015, Apr. 9-12, 2015, (6 pages), Fort Lauderdale, Florida.

Kenford, Susan L. et al. "Predicting Smoking Cessation. Who Will Quit With and Without the Nicotine Patch," JAMA, Feb. 23, 1994, vol. 271, No. 8, pp. 589-594.

McLernon, F. Joseph et al. "I Am Your Smartphone, and I Know You Are About to Smoke: The Application of Mobile Sensing and Computing Approaches to Smoking Research and Treatment," Nicotine and Tobacco Research, (2013), vol. 15, No. 10, pp. 1651-1654.

Nahum-Shani Inbal et al. "Just-in-Time Adaptive Interventions (JITAIs): An Organizing Framework for Ongoing Health Behavior Support," The Methodology Center Technical Report No. 14-126, (2014), pp. 1-37, University Park, PA, Penn State.

Naughton, Felix et al. "A Context-Sensing Mobile Phone App (Q Sense) for Smoking Cessation: A Mixed-Methods Study," JMIR Mhealth and Uhealth, (2016), vol. 4, Issue 3, e106, pp. 1-13. DOI: 10.2196/mhealth.5787.

Naughton, Felix. "Delivering 'Just-In-Time' Smoking Cessation Support Via Mobile Phones: Current Knowledge and Future Direction," Nicotine & Tobacco Research: Official Journal of the Society for Research on Nicotine and Tobacco, (2016), (12 pages).

Paay, Jeni et al. "QuittyLink: Using Smartphones for Personal Counseling to Help People Quit Smoking," MobileHCI'15, Aug. 24-27, 2015, pp. 98-104, Copenhagen, Denmark.

Saleheen, Nazir et al. "puffMarker: A Multi-Sensor Approach for Pinpointing the Timing of First Lapse in Smoking Cessation," InProceedings of the 2015 ACM International Joint Conference on Pervasive and Ubiquitous Computing, Sep. 2015, pp. 999-1010. DOI: 10.1145/2750858.2806897.

Sarker, Hillol et al. "Finding Significant Stress Episodes in a Discontinuous Time Series of Rapidly Varying Mobile Sensor Data," InProceedings of the 2016 CHI Conference on Human Factors in Computing Systems, May 7, 2016, pp. 4489-4501. DOI: 10.1145/2858036.2858218.

Sarker, Hillol et al. "From Markers to Interventions: The Case of Just-In-Time Stress Intervention," InMobile Health, (2017), pp. 411-433, Springer International Publishing AG, Cham, Switzerland. DOI: 10.1007/978-3-319-51394-2_21.

Ward Marcia M. Self-Reported Abstinence Effects in the First Month After Smoking Cessation. Addictive Behaviors, (2001), vol. 26, No. 3, pp. 311-327.

* cited by examiner

US 12,236,320 B2

PASSIVE HEIGHTENED NEED PREDICTION

BACKGROUND

Various embodiments of the present invention address technical challenges related to performing heightened need prediction. Various embodiments of the present invention address the shortcomings of existing heightened need prediction systems and disclose various techniques for efficiently and reliably performing heightened need prediction.

BRIEF SUMMARY

In general, embodiments of the present invention provide methods, apparatus, systems, computing devices, computing entities, and/or the like for performing passive heightened need prediction. Certain embodiments utilize systems, methods, and computer program products that perform performing passive heightened need prediction by utilizing at least one of heighted need prediction machine learning models, offline training of heightened need prediction machine learning models, online training of heightened need machine learning models, hybrid training of heightened need machine learning models, and optimal action determination models.

In accordance with one aspect, a method is provided. In one embodiment, the method comprises, during an online prediction phase, receiving incoming monitoring data associated with the user profile; performing anomaly reduction on the incoming monitoring data to generate anomaly-reduced incoming monitoring data; generating an incoming monitoring window based on the anomaly-reduced incoming monitoring data; processing the incoming monitoring window using a trained heightened need prediction machine learning model to determine a heightened need prediction for the incoming monitoring window; and in response to determining that the heightened need prediction is positive, performing one or more responsive actions by communicating with one or more client devices associated with the user profile.

In accordance with another aspect, a computer program product is provided. The computer program product may comprise at least one computer-readable storage medium having computer-readable program code portions stored therein, the computer-readable program code portions comprising executable portions configured to, during an online prediction phase, receive incoming monitoring data associated with the user profile; performing anomaly reduction on the incoming monitoring data to generate anomaly-reduced incoming monitoring data; generate an incoming monitoring window based on the anomaly-reduced incoming monitoring data; process the incoming monitoring window using a trained heightened need prediction machine learning model to determine a heightened need prediction for the incoming monitoring window; and in response to determining that the heightened need prediction is positive, perform one or more responsive actions by communicating with one or more client devices associated with the user profile.

In accordance with yet another aspect, an apparatus comprising at least one processor and at least one memory including computer program code is provided. In one embodiment, the at least one memory and the computer program code may be configured to, with the processor, cause the apparatus to, during an online prediction phase, receive incoming monitoring data associated with the user profile; performing anomaly reduction on the incoming monitoring data to generate anomaly-reduced incoming monitoring data; generate an incoming monitoring window based on the anomaly-reduced incoming monitoring data; process the incoming monitoring window using a trained heightened need prediction machine learning model to determine a heightened need prediction for the incoming monitoring window; and in response to determining that the heightened need prediction is positive, perform one or more responsive actions by communicating with one or more client devices associated with the user profile.

BRIEF DESCRIPTION OF THE DRAWINGS

Figure 1:
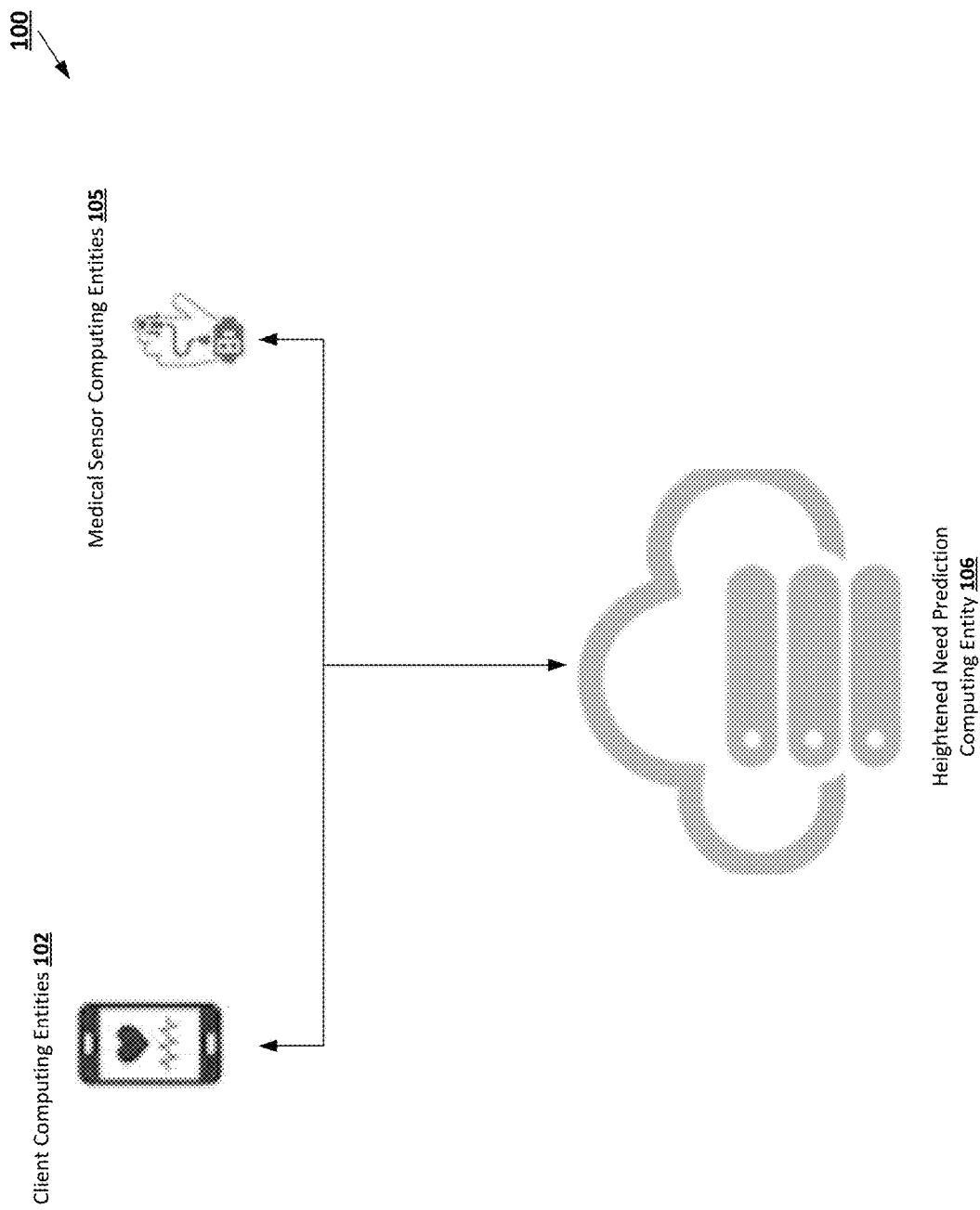

Having thus described the invention in general terms, reference will now be made to the accompanying drawings, which are not necessarily drawn to scale, and wherein:

FIG. 1 provides an exemplary overview of an architecture that can be used to practice embodiments of the present invention.

Figure 2:
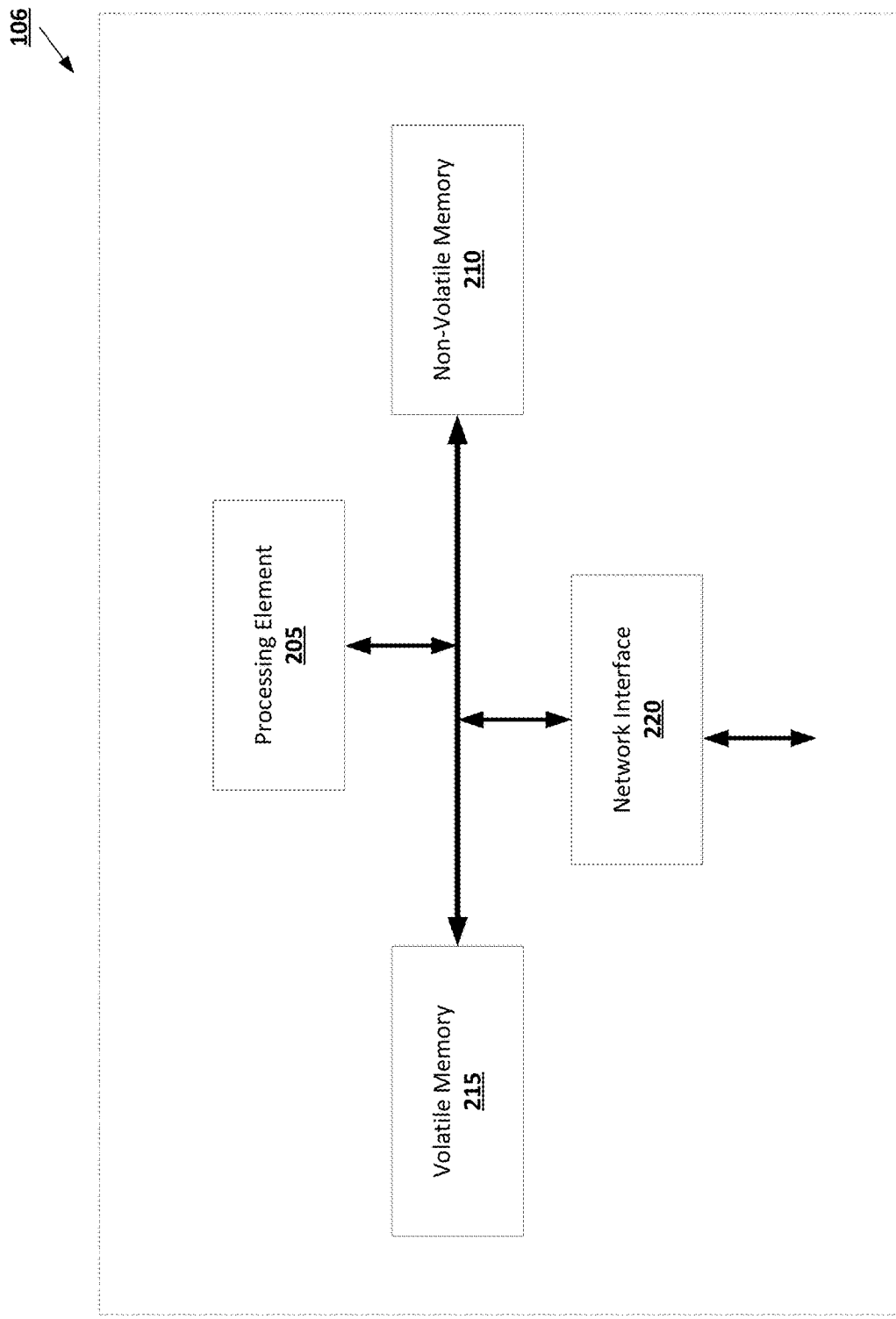

FIG. 2 provides an example heightened need prediction computing entity in accordance with some embodiments discussed herein.

Figure 3:
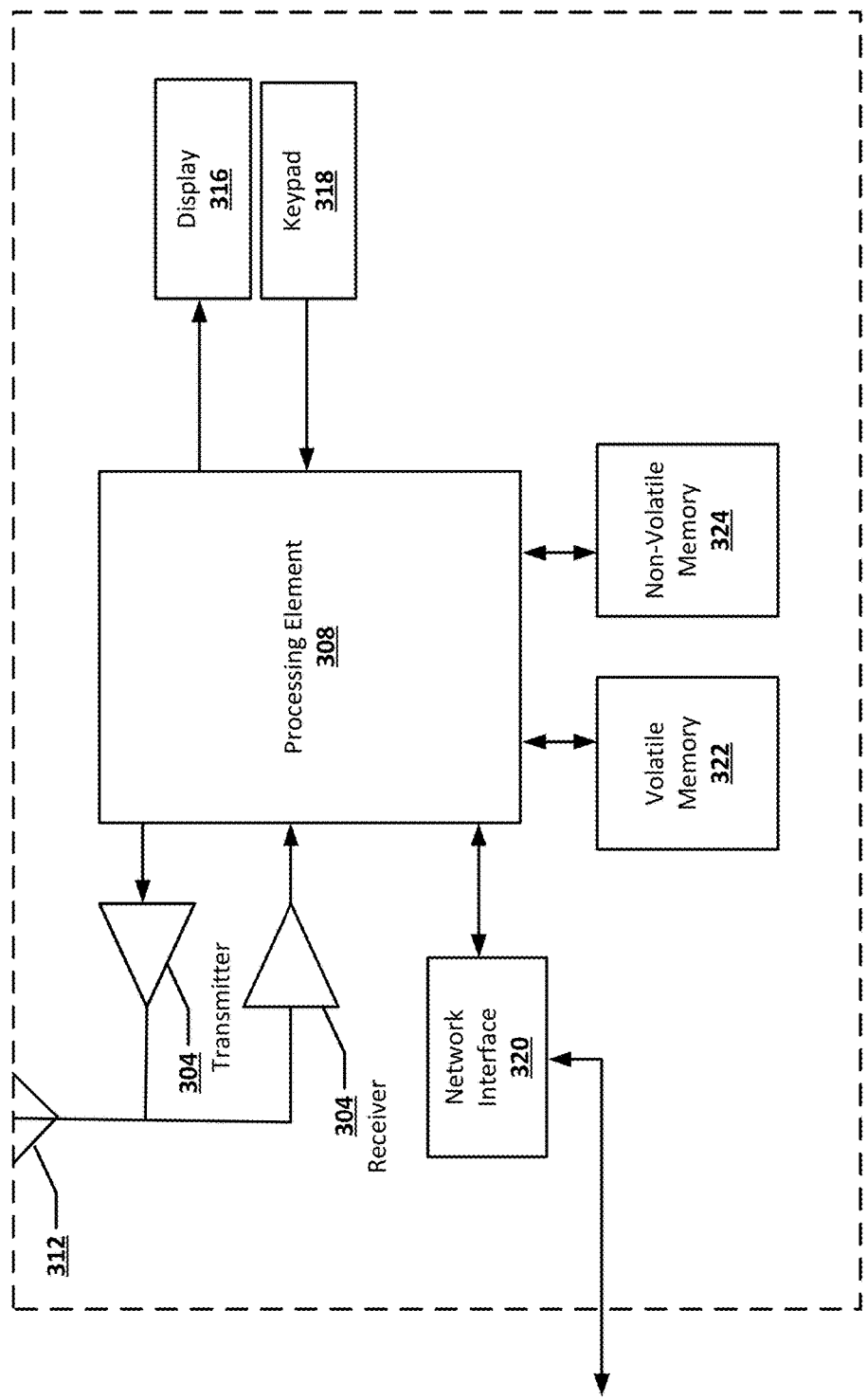

FIG. 3 provides an example client computing entity in accordance with some embodiments discussed herein.

Figure 4:
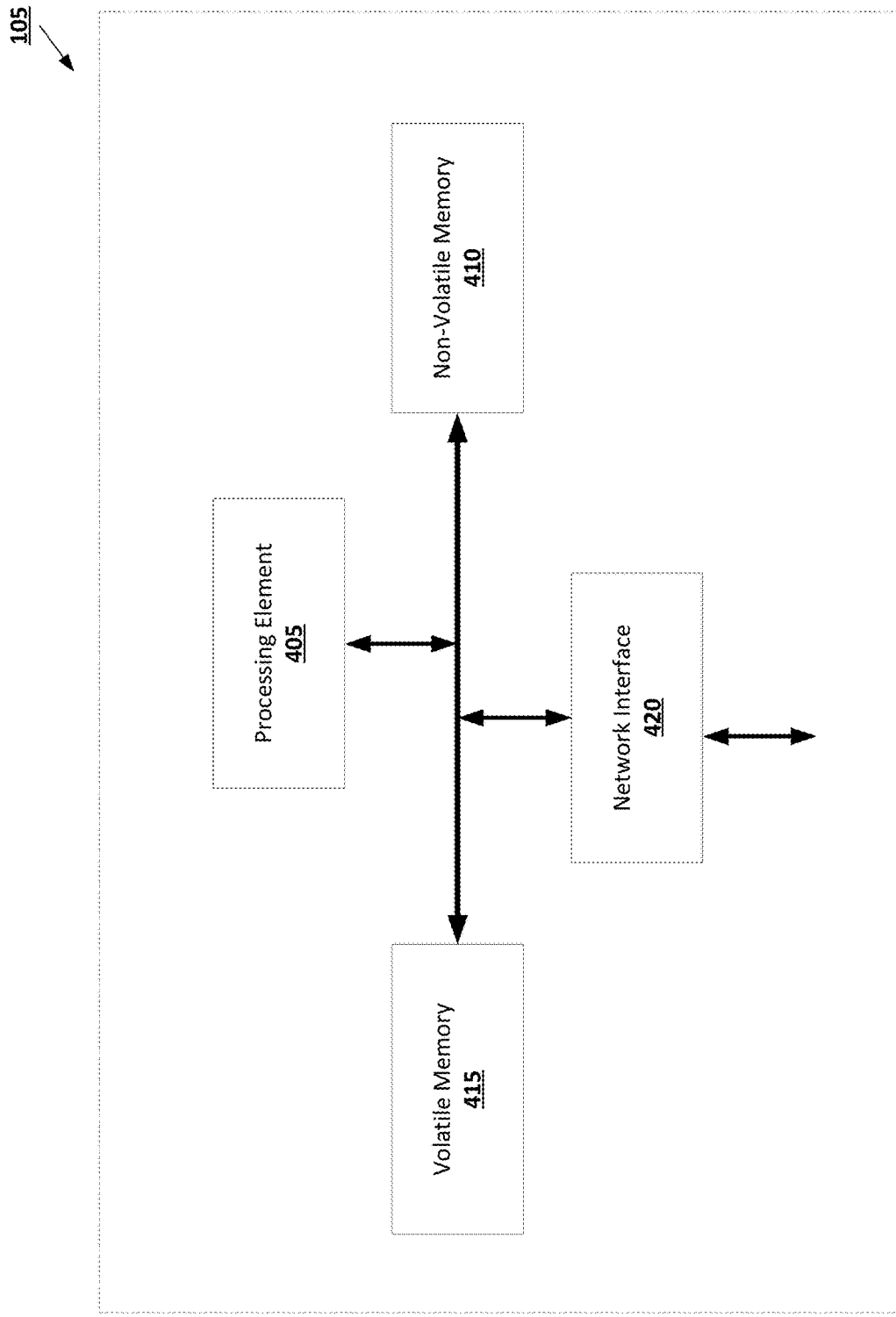

FIG. 4 provides an example sensor computing entity in accordance with some embodiments discussed herein.

Figure 5:
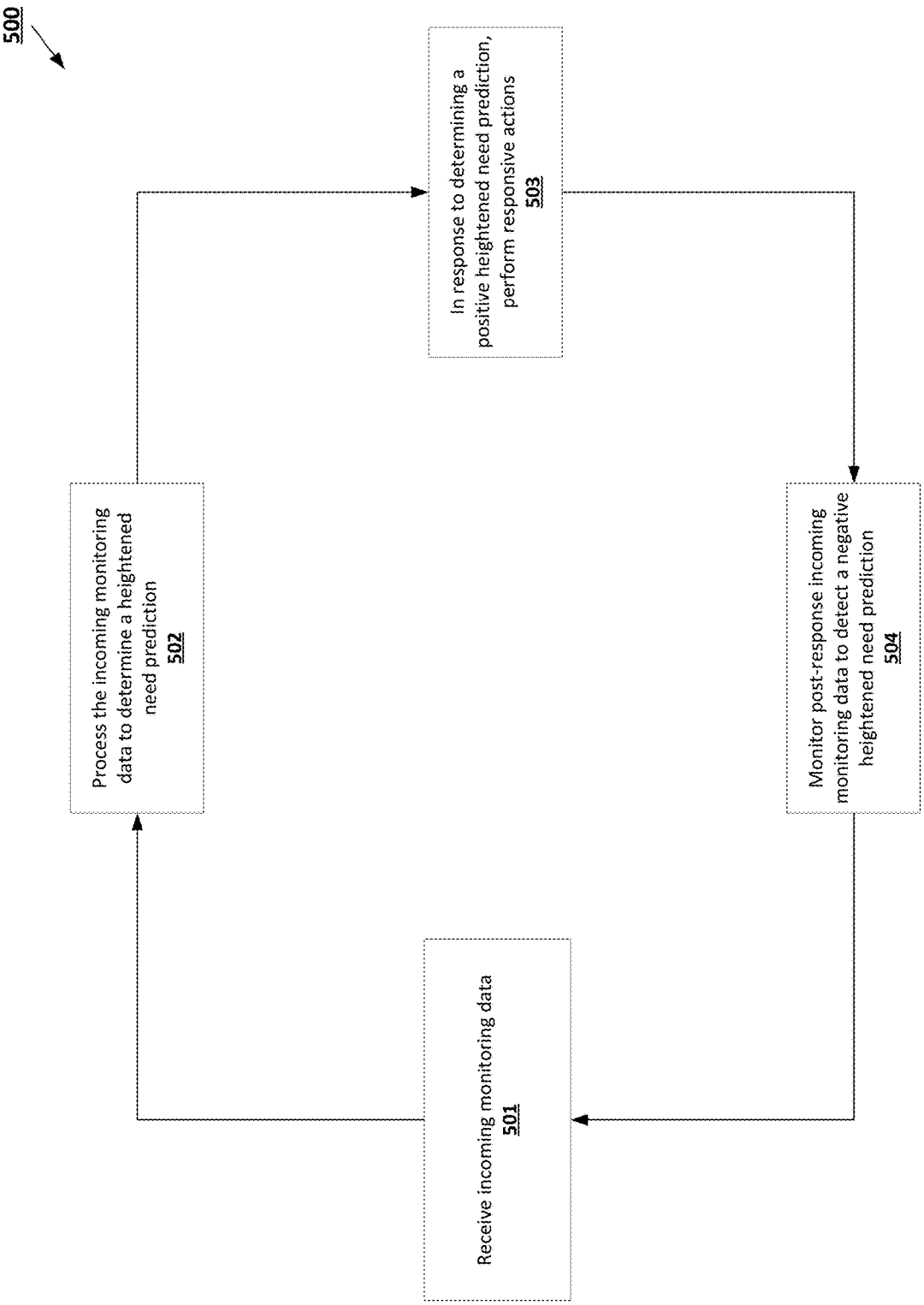

FIG. 5 is a flowchart diagram of an example process for performing passive heightened need prediction for a user profile in accordance with some embodiments discussed herein.

Figure 6:
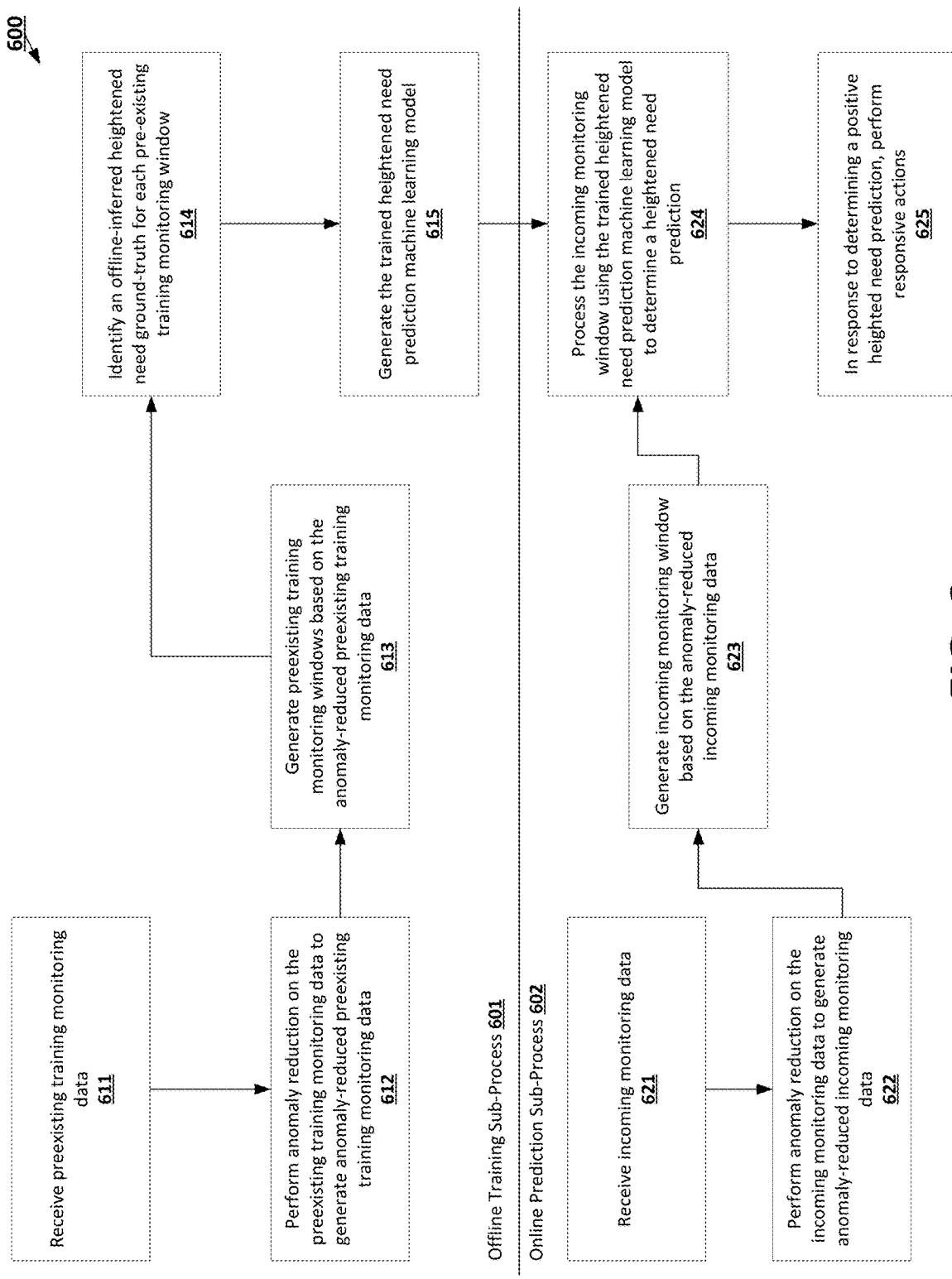

FIG. 6 is a flowchart diagram of an example process for performing passive heightened need prediction for a user profile using an offline-trained heightened need prediction machine learning model in accordance with some embodiments discussed herein.

Figure 7:
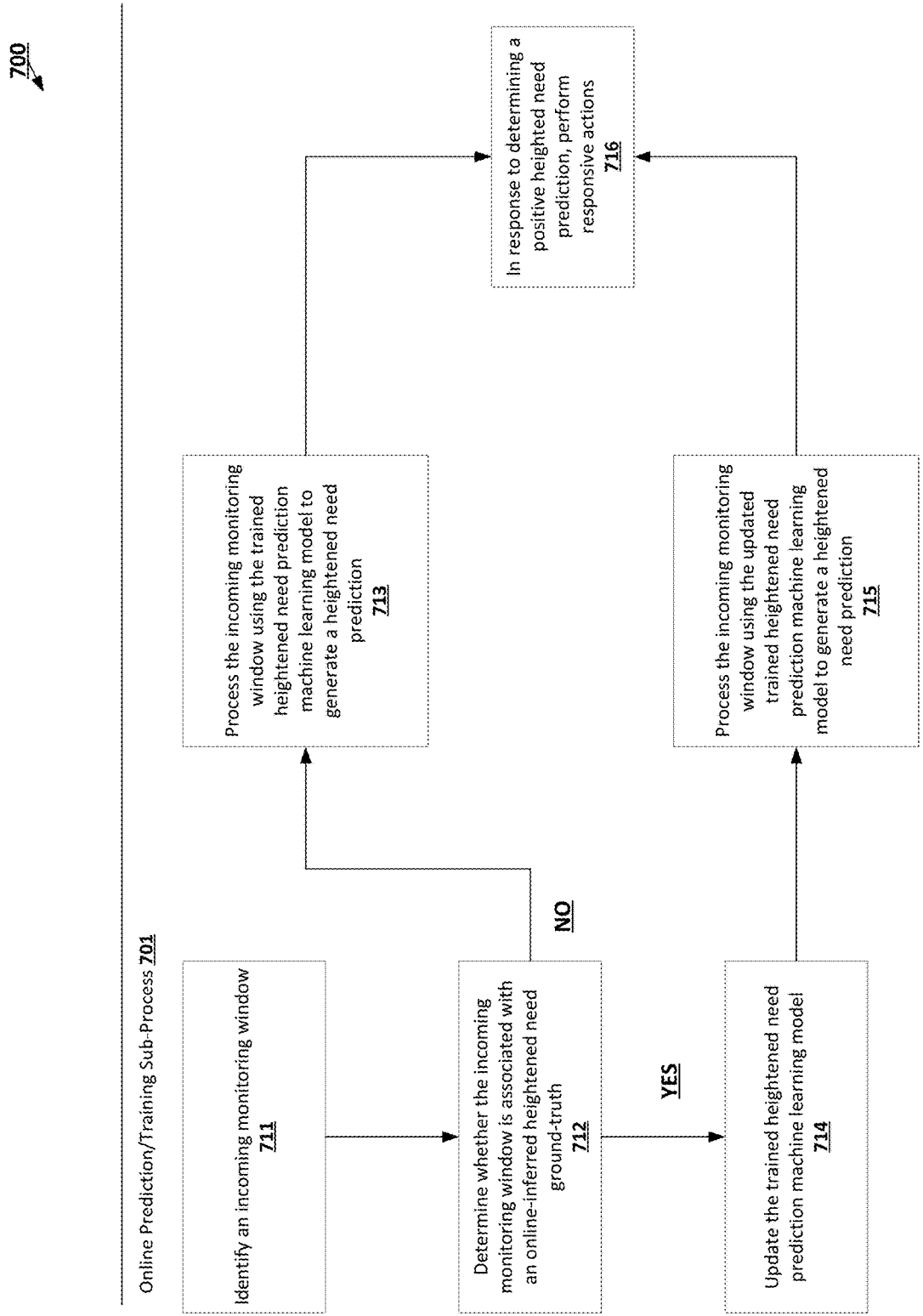

FIG. 7 is a flowchart diagram of an example process for performing passive heightened need prediction for a user profile using an online-trained heightened need prediction machine learning model in accordance with some embodiments discussed herein.

Figure 8:
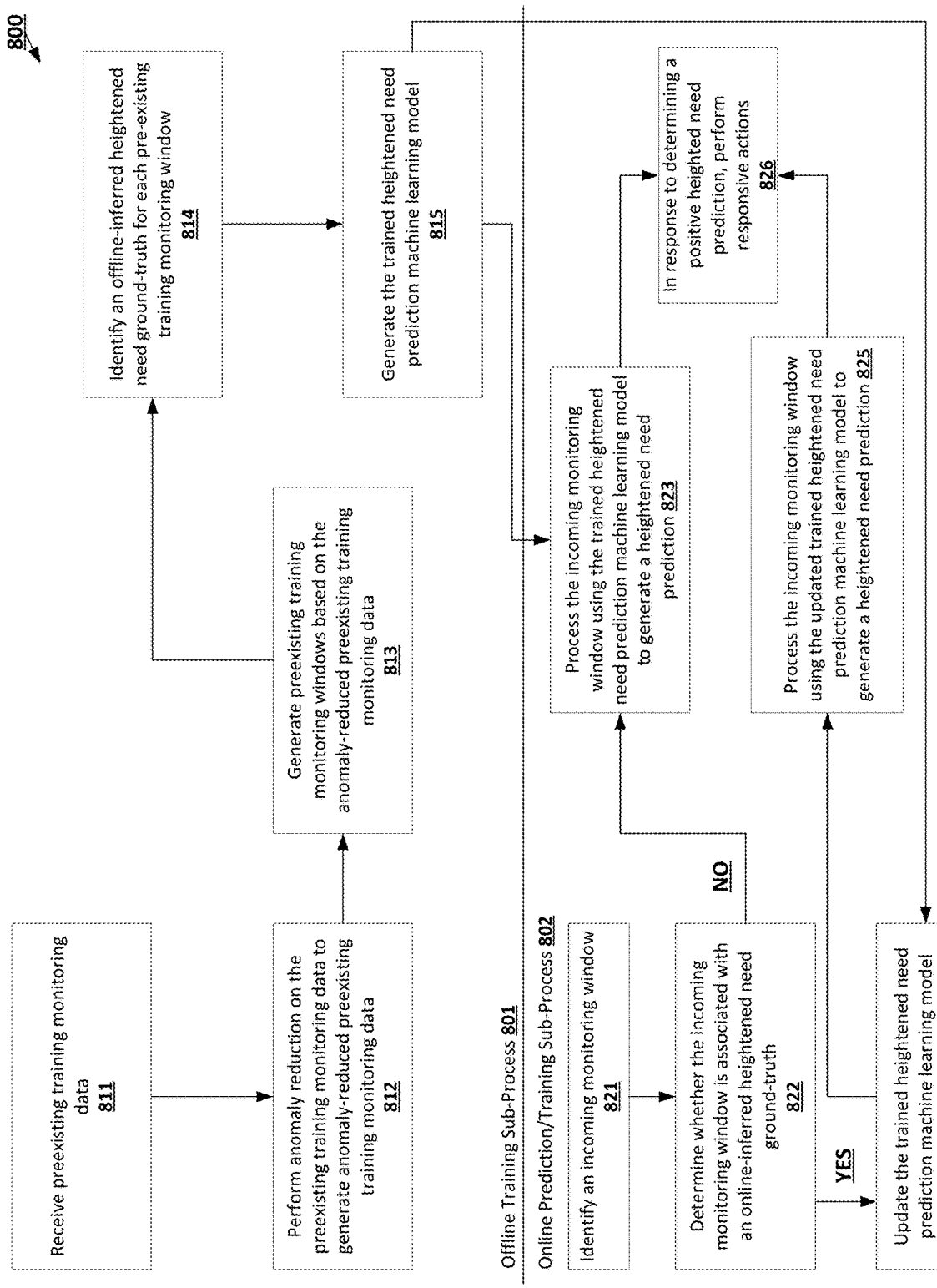

FIG. 8 is a flowchart diagram of an example process for performing passive heightened need prediction for a user profile using a hybrid-trained heightened need prediction machine learning model in accordance with some embodiments discussed herein.

Figure 9:
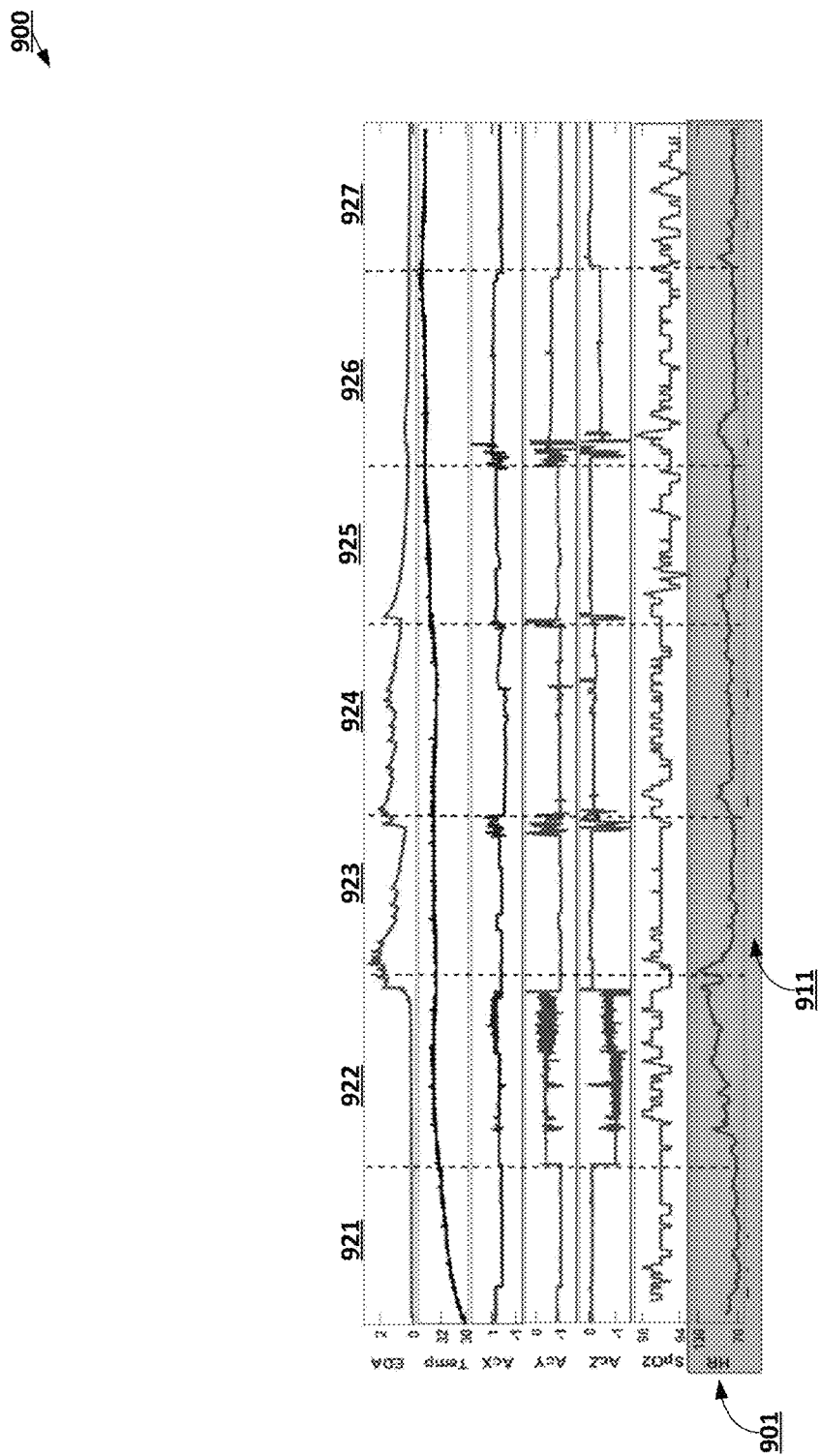

FIG. 9 provides an operational example of a monitoring data object in accordance with some embodiments discussed herein.

Figure 10:

FIG. 10 provides an operational example of a heightened need prediction data object in accordance with some embodiments discussed herein.

Figure 11:
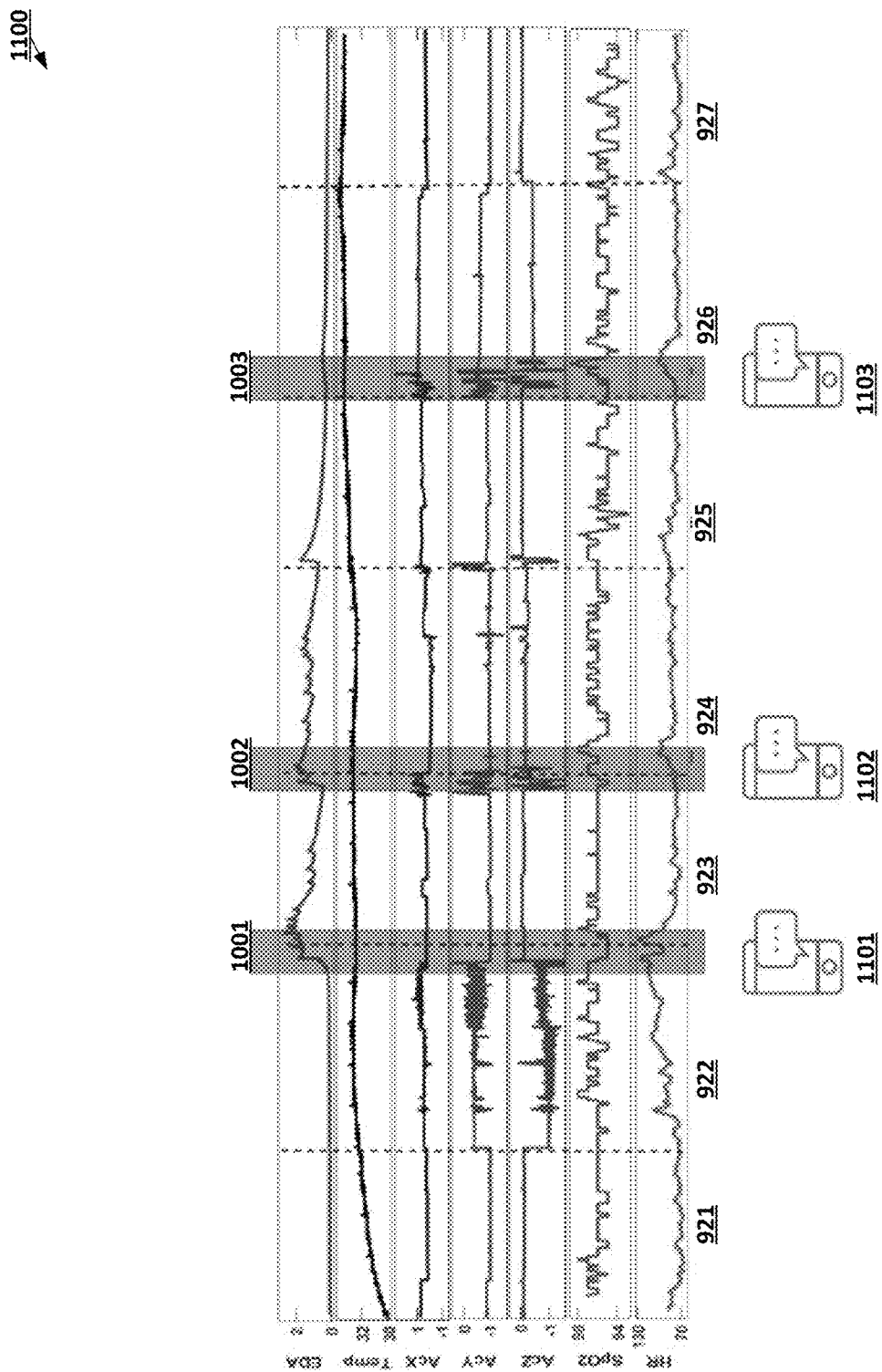

FIG. 11 provides an operational example of an optimal action determination data object in accordance with some embodiments discussed herein.

Figure 12:
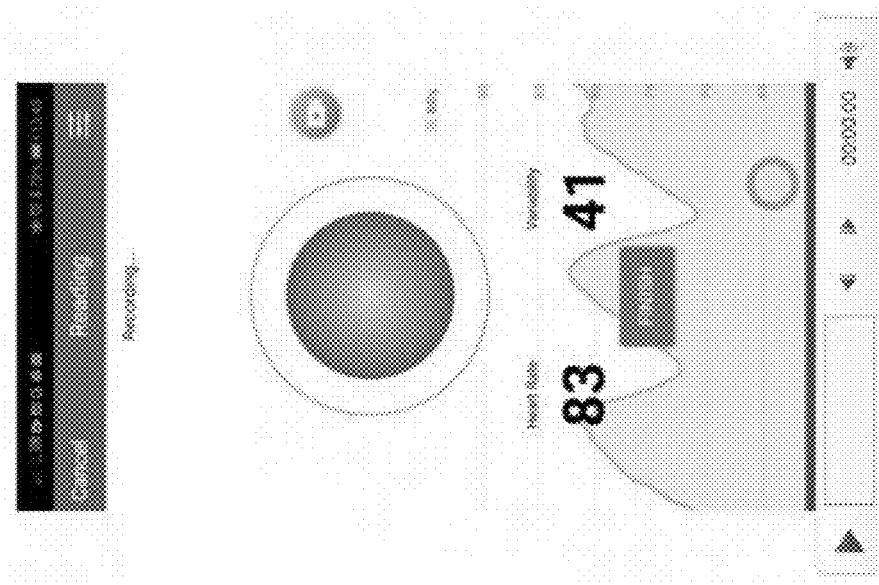

FIG. 12 provides an operational example of a responsive action user interface in accordance with some embodiments discussed herein.

DETAILED DESCRIPTION

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis.

I. OVERVIEW

Various embodiments of the present invention disclose techniques for reliably and efficiently performing user condition monitoring (e.g., heightened need prediction) that creatively utilize machine learning models to reduce the computational complexity and the storage complexity of performing such user condition monitoring actions. The machine learning techniques used herein to perform user condition monitoring are designed to have an asymmetric cost profile, a property that causes much of the costs of user condition monitoring performed using the noted machine learning models to be shifted to training time, which in turn reduces the amount of computations and/or the amount of model-definition data needed to perform effective and reliable user condition monitoring post-training.

Furthermore, various embodiments of the present invention disclose techniques for training user condition monitoring machine learning models (e.g., heightened need detection machine learning models) that enable a hybrid of both offline training and online training. The resulting models are incredibly versatile and powerful, as they are both able to capture important preexisting predictive signals via offline training as well as dynamically-changing predictive signals via online training. In addition, integration of preexisting predictive signals reduces the amount of computationally-costly online learning operations that need to be performed before the models reach a sufficient level of reliability and accuracy.

II. EXEMPLARY DEFINITIONS

The term "online prediction phase" may refer to a data object that describes configuration parameters for operation of a heightened need prediction computing entity during a period in which the heightened need prediction computing entity is configured to determine one or more heightened need predictions for a user profile based on incoming monitoring data associated with the user profile and by using a trained heightened need prediction machine learning model. In some embodiments, the time period described by the online prediction phase may be preceded by a time period described by an offline training phase. In some embodiments, the time period described by the online prediction phase may also comprise generating or updating the trained heightened need prediction machine learning model based on incoming training monitoring data associated with the user profile.

The term "offline training phase" may refer to a data object that describes configuration parameters for the operation of the heightened need prediction computing entity during a time period prior to the time period described by the online prediction phase in which the heightened need prediction computing entity is configured to generate the trained heightened need prediction machine learning model based on training monitoring data associated with the user profile.

The term "incoming monitoring data" may refer to a collection of one or more data objects that describe information about one or more recorded conditions and/or one or more recorded activities of an end user associated with the user profile during a current time interval of the online prediction phase. For example, the incoming monitoring data may include one or more data objects that describe one or more recorded physiological conditions (e.g., a blood pressure, a heart rate, an electrocardiogram, a breathing rate, an acceleration rate, a galvanic skin response, a body temperature, a beating rate, an electromyogram, an electroencephalogram, a blood oxygen, and/or the like) of the end user associated with the user profile during the current time interval of the online prediction phase. As another example, the incoming monitoring data may include one or more data objects that describe one or more behavioral conditions (e.g., one or more arm movements, one or more eye movement patterns, an eye blinking rate, a bone reflex speed, and/or the like) of the end user associated with the user profile during a current time interval of the online prediction phase. As yet another example, the incoming monitoring data may include one or more location markers for the end user associated with the user profile during a current time interval of the online prediction phase. As a further example, the incoming monitoring data may include one or more data objects that describe one or more facial features of the end user associated with the user profile during a current time interval of the online prediction phase.

The term "incoming monitoring window" may refer to a data object that describes a subset of the incoming monitoring data that is deemed to be temporally adequate (e.g., lengthy enough) for use in order to determine whether the end user associated with the user profile is experiencing a heightened need condition during the incoming monitoring window. For example, configuration data for a heightened need prediction computing entity may require that the incoming monitoring data be divided into disjoint or overlapping subsets each associated with a predefined length of time (e.g., five seconds of time), and that each subset be deemed an incoming monitoring window. As another example, configuration data for a heightened need prediction computing entity may require that the incoming monitoring data be divided into disjoint or overlapping subsets each defined based on proximity to a detected user action (e.g., to a detected deep-breathing action), and that each disjoint subset be deemed an incoming monitoring window. In some embodiments, to determine the incoming monitoring window, a heightened need prediction computing entity performs anomaly reduction on the incoming monitoring data to generate anomaly-reduced incoming monitoring data and determines the incoming monitoring window based on the anomaly-reduced incoming monitoring data.

The term "heightened need prediction" may refer to data object that describes an estimated determination about whether a corresponding incoming monitoring window describes a period of time in which the need for a target activity and/or a target substance by the end user associated with the user profile is beyond an ordinary level of need for the target activity and/or the target substance. Examples of heightened need conditions that characterize heightened need periods include craving conditions, such as cravings for nicotine, for sugar, for particular addictive behaviors, and/or the like. In some embodiments, to determine the heightened need prediction for a corresponding incoming monitoring window, a heightened need prediction computing entity processes the incoming monitoring window using a trained heightened need prediction machine learning model to determine the heightened need prediction for the incoming monitoring window.

The term "optimal need-reducing action" may refer to a data object that describes a real-world action configured to be performed by an end user associated with the user profile, where the real-world action is configured to be most adapted to lessen a predicted level of need for a target activity and/or a target substance by the end user. The optimal need-reducing action may be selected from a list of candidate need-reducing actions based on at least one of subject matter domain data, configuration data associated with a client device for the user profile, historical data about past efficacy of responsive actions performed by the user profile in reducing need levels during heightened need periods, and/or the like. In some embodiments, to determine the optimal need-reducing action for the user profile, a heightened need prediction computing entity utilizes an optimal action determination model, such as a trained optimal action determination model.

The term "post-response incoming monitoring data" may refer to incoming monitoring data associated with a time interval that occurs subsequent to performing responsive actions in response to detecting a positive heightened need prediction. For example, the post-response incoming monitoring data may be associated with a time interval that occurs immediately after performing responsive actions in response to detecting a positive heightened need prediction. As another example, the post-response incoming monitoring data may be associated with a time interval that occurs immediately after the passage of an expected reactive latency period after performing responsive actions in response to detecting a positive heightened need prediction, where the expected reactive latency period may include an expected time interval required for performing the optimal need-reducing action associated with the responsive actions.

The term "post-response incoming monitoring window" may refer to a data object that describes a subset of the post-response incoming monitoring data that is deemed to be temporally adequate (e.g., lengthy enough) to use in order to determine whether the end user associated with the user profile is experiencing a heightened need condition. For example, configuration data for a heightened need prediction computing entity may require that the post-response incoming monitoring data be divided into disjoint subsets each associated with a predefined length of time (e.g., five seconds of time), and that each disjoint subset be deemed a post-response incoming monitoring window. As another example, configuration data for heightened need prediction computing entity may require that the post-response incoming monitoring data be divided into disjoint or overlapping subsets each defined based on proximity to a detected user action (e.g., to a detected deep-breathing action), and that each disjoint subset be deemed a post-response incoming monitoring window. In some embodiments, to determine a post-response incoming monitoring window, a heightened need prediction computing entity performs anomaly reduction on the post-response incoming monitoring data to generate anomaly-reduced post-response incoming monitoring data and determines the post-response incoming monitoring window based on the anomaly-reduced post-response incoming monitoring data.

The term "preexisting training monitoring data" may refer to a collection of one or more data objects that describe information about one or more recorded conditions and/or one or more recorded activities of an end user associated with the user profile during a past time interval associated with the offline training phase, where the collection of one or more data objects are associated with one or more heightened need ground-truths. For example, the preexisting training monitoring data may include one or more data objects that describe one or more recorded physiological conditions (e.g., a blood pressure, a heart rate, an electrocardiogram, a breathing rate, an acceleration rate, a galvanic skin response, a body temperature, a beating rate, an electromyogram, an electroencephalogram, a blood oxygen, and/or the like) of the end user associated with the user profile during the past time interval associated with the offline training phase. As another example, the preexisting training monitoring data may include one or more data objects that describe one or more behavioral conditions (e.g., one or more arm movements, one or more eye movement patterns, an eye blinking rate, a bone reflex speed, and/or the like) of the end user associated with the user profile during the past time interval associated with the offline training phase. As yet another example, the preexisting training monitoring data may include one or more location markers for the end user associated with the user profile during the current time interval of the online prediction phase. As a further example, the incoming monitoring data may include one or more data objects that describe one or more facial features of the end user associated with the user profile during the past time interval associated with the offline training phase.

The term "offline-inferred heightened need prediction" may refer to a data object that describes a heightened need prediction for a corresponding preexisting training monitoring window, where the noted heightened need prediction is determined as part of the process of training/updating a heightened need prediction machine learning model during the offline training stage for the heightened need prediction machine learning model. In other words, the offline-inferred heightened need prediction is a data object that describes a heightened need prediction generated during the process of training/updating a heightened need prediction machine learning model during the offline training stage for the heightened need prediction machine learning model.

The term "offline-inferred heightened need ground-truth" may refer to a data object that describes information about whether a corresponding preexisting training monitoring window describes a heightened need condition based on real-world data describing end user intentions and/or end user actions during the time interval associated with the corresponding preexisting training monitoring window, where the noted information are obtained during the online training stage for a corresponding heightened need prediction machine learning model. For example, the offline-inferred heightened need ground-truth may be determined based on direct user input describing that the user is experiencing a craving condition at a time associated with inputting the direct user input. As another example, the offline-inferred heightened need ground-truth may describe that a target end user is engaging in a need response action at a time associated with the corresponding preexisting training monitoring window for the offline-inferred heightened need ground-truth, where the need response action may be a data object that describes an action expected to be performed in response to a heightened need condition, such as a cigarette smoking action.

The term "online-inferred heightened need prediction" may refer to a data object that describes a heightened need prediction for a corresponding incoming monitoring window that is generated using a trained heightened need prediction machine learning model prior to updating/retraining of the trained heightened need prediction machine learning model based on a deviation measure between the online-inferred heightened need prediction for the incoming monitoring window and the online-inferred heightened need ground-truth for the incoming monitoring window.

The term "online-inferred heightened need ground-truth" may refer to a data object that describes information about whether a corresponding incoming monitoring window describes a heightened need condition based on real-world data describing end user intentions and/or end user actions during the time interval associated with the corresponding preexisting training monitoring window, where the real-world data are obtained during the online prediction stage for a corresponding heightened need prediction machine learning model. For example, the online-inferred heightened need ground-truth may be determined based on direct user input describing that the user is experiencing a craving condition at a time associated with inputting the direct user input. As another example, the online-inferred heightened need ground-truth may describe that a target end user is engaging in a need response action at a time associated with the corresponding incoming monitoring window for the online-inferred heightened need ground-truth, where the need response action may be a data object that describes an action expected to be performed in response to a heightened need condition, such as a cigarette smoking action.

The term "heightened need prediction machine learning model" may refer to a data object that describes parameters and/or hyperparameters of a machine learning model configured to predict, based on a monitoring data window, whether the monitoring data window includes a heightened need condition. The heightened need prediction may be trained in accordance with at least one of the processes described with reference to FIGS. 6-9. The heightened need prediction machine learning model may include at least one of the following: (i) non-sequential models (e.g. Support Vector Machines, Random Forests, Multi-Level Perceptron models, Gradient Boosting Machines, and/or the like); (ii) one-dimensional convolutional neural network models configured to predict lapse likelihood as a function of the sequences of signals in the windowed data; and (iii) sequential neural networks (Recurrent Neural Networks, Gated Recurrent Unit, Long-Short Term Memory models) configured to predict lapse likelihood as a function of the sequences of signals in the windowed data.

The term "optimal action determination model" may refer to a data object that describes parameters and/or hyperparameters of a model (e.g., a machine learning model) that is configured to determine the optimal need-reducing action for a monitoring window that has a positive heightened need prediction. In some embodiments, the optimal action determination is associated with one or more trained parameters, where the trained parameters of the optimal action determination model may define a generalized linear model that is configured to receive as inputs at least one of the following: (i) one or more input variables describing past behavioral patterns of a target end user in relation to different candidate need-reducing actions, (ii) one or more input variables describing past behaviors of a community of end users addicted to a target need-inducing activity and/or a target need-inducing substance (e.g., a target addictive activity and/or a target addictive substance) in relation to different candidate need-reducing actions, (iii) one or more technological capabilities of the target end user in relation to different candidate need-reducing actions (e.g., whether a smartphone device of the target end user enables particular need-reducing actions), (iv) one or more environmental conditions/constraints of the target end user in relation to different candidate need-reducing actions, and (iv) one or more time conditions/constraints of the target end user in relation to different candidate need-reducing actions.

III. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a dataset query or search language, and/or a report writing language. In one or more example embodiments, a software component comprising instructions in one of the foregoing examples of programming languages may be executed directly by an operating system or other software components without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. EXEMPLARY SYSTEM ARCHITECTURE

FIG. 1 is a schematic diagram of an example architecture 100 for performing heightened need prediction. The architecture 100 includes a heightened need prediction computing entity 106 configured to detect heightened need conditions (e.g., conditions in which a user craves smoking) based on data provided by sensor computing entities 105 and/or client computing devices 102. Moreover, the heighted need prediction computing entity 106 may be configured to select need-reducing actions (e.g., computer-assisted psychological exercises) in response to detected heightened need conditions and cause the client computing entities 102 to perform/present the need-reducing actions.

In some embodiments, the heightened need prediction computing entity 106 may communicate with at least one of the client computing entities 102 and/or at least one of the sensor computing entities 105 using one or more communication networks, such as the communication network 104. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The heightened need prediction computing entity 106 may include a storage subsystem configured to store configuration data and/or training data utilized by the heightened need prediction computing entity 106. The storage subsystem may include one or more storage units, such as multiple distributed storage units that are connected through a computer network. Each storage unit in the storage subsystem may store at least one of one or more data assets and/or one or more data about the computed properties of one or more data assets. Moreover, each storage unit in the storage subsystem may include one or more non-volatile storage or memory media including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Heightened Need Prediction Computing Entity

FIG. 2 provides a schematic of a heightened need prediction computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the heightened need prediction computing entity 106 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the heightened need prediction computing entity 106 may include or be in communication with one or more processing elements 205 (also referred to as processors, processing circuitry, and/or similar terms used herein interchangeably) that communicate with other elements within the heightened need prediction computing entity 106 via a bus, for example. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the heightened need prediction computing entity 106 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. As will be recognized, the non-volatile storage or memory media may store datasets, dataset instances, dataset management systems, data, applications, programs, program modules, scripts, source code, object code, byte code, compiled code, interpreted code, machine code, executable instructions, and/or the like. The term dataset, dataset instance, dataset management system, and/or similar terms used herein interchangeably may refer to a collection of records or data that is stored in a computer-readable storage medium using one or more dataset models, such as a hierarchical dataset model, network model, relational model, entity-relationship model, object model, document model, semantic model, graph model, and/or the like.

In one embodiment, the heightened need prediction computing entity 106 may further include or be in communication with volatile media (also referred to as volatile storage, memory, memory storage, memory circuitry and/or similar terms used herein interchangeably). In one embodiment, the volatile storage or memory may also include one or more volatile storage or memory media 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. As will be recognized, the volatile storage or memory media may be used to store at least portions of the datasets, dataset instances, dataset management systems, data, applications, programs, program modules, scripts, source code, object code, byte code, compiled code, interpreted code, machine code, executable instructions, and/or the like being executed by, for example, the processing element 205. Thus, the datasets, dataset instances, dataset management systems, data, applications, programs, program modules, scripts, source code, object code, byte code, compiled code, interpreted code, machine code, executable instructions, and/or the like may be used to control certain aspects of the operation of the heightened need prediction computing entity 106 with the assistance of the processing element 205 and operating system.

As indicated, in one embodiment, the heightened need prediction computing entity 106 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the heightened need prediction computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the heightened need prediction computing entity 106 may include or be in communication with one or more input elements, such as a keyboard input, a mouse input, a touch screen/display input, motion input, movement input, audio input, pointing device input, joystick input, keypad input, and/or the like. The heightened need prediction computing entity 106 may also include or be in communication with one or more output elements (not shown), such as audio output, video output, screen/display output, motion output, movement output, and/or the like.

Exemplary Client Computing Entity

FIG. 3 provides an illustrative schematic representative of a client computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Client computing entities 102 can be operated by various parties. As shown in FIG. 3, the client computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the client computing entity 102 may be capable of operating with one or more air interface standards, communication protocols, modulation types, and access types. More particularly, the client computing entity 102 may operate in accordance with any of a number of wireless communication standards and protocols, such as those described above with regard to the heightened need prediction computing entity 106. In a particular embodiment, the client computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the client computing entity 102 may operate in accordance with multiple wired communication standards and protocols, such as those described above with regard to the heightened need prediction computing entity 106 via a network interface 320.

Via these communication standards and protocols, the client computing entity 102 can communicate with various other entities using concepts such as Unstructured Supplementary Service Data (USSD), Short Message Service (SMS), Multimedia Messaging Service (MIMS), Dual-Tone Multi-Frequency Signaling (DTMF), and/or Subscriber Identity Module Dialer (SIM dialer). The client computing entity 102 can also download changes, add-ons, and updates, for instance, to its firmware, software (e.g., including executable instructions, applications, program modules), and operating system.

According to one embodiment, the client computing entity 102 may include location determining aspects, devices, modules, functionalities, and/or similar words used herein interchangeably. For example, the client computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the client computing entity's 102 position in connection with a variety of other systems, including cellular towers, Wi-Fi access points, and/or the like. Similarly, the client computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The client computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the client computing entity 102 to interact with and/or cause display of information/data from the heightened need prediction computing entity 106, as described herein. The user input interface can comprise any of a number of devices or interfaces allowing the client computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the client computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The client computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store datasets, dataset instances, dataset management systems, data, applications, programs, program modules, scripts, source code, object code, byte code, compiled code, interpreted code, machine code, executable instructions, and/or the like to implement the functions of the client computing entity 102. As indicated, this may include a user application that is resident on the entity or accessible through a browser or other user interface for communicating with the heightened need prediction computing entity 106 and/or various other computing entities.

In another embodiment, the client computing entity 102 may include one or more components or functionality that are the same or similar to those of the heightened need prediction computing entity 106, as described in greater detail above. As will be recognized, these architectures and descriptions are provided for exemplary purposes only and are not limiting to the various embodiments.

In various embodiments, the client computing entity 102 may be embodied as an artificial intelligence (AI) computing entity, such as an Amazon Echo, Amazon Echo Dot, Amazon Show, Google Home, and/or the like. Accordingly, the client computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

Exemplary Sensor Computing Entity

FIG. 4 provides a schematic of a sensor computing entity 105 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the heightened need prediction computing entity 106 may also include one or more communications interfaces 420 for communicating with various computing entities, such as by communicating data, content, information, and/or similar terms used herein interchangeably that can be transmitted, received, operated on, processed, displayed, stored, and/or the like.

As shown in FIG. 4, in one embodiment, the heightened need prediction computing entity 106 may include or be in communication with one or more processing elements 405 (also referred to as processors, processing circuitry, and/or similar terms used herein interchangeably) that communicate with other elements within the heightened need prediction computing entity 106 via a bus, for example. As will be understood, the processing element 405 may be embodied in a number of different ways. For example, the processing element 405 may be embodied as one or more complex programmable logic devices (CPLDs), microprocessors, multi-core processors, coprocessing entities, application-specific instruction-set processors (ASIPs), microcontrollers, and/or controllers. Further, the processing element 405 may be embodied as one or more other processing devices or circuitry. The term circuitry may refer to an entirely hardware embodiment or a combination of hardware and computer program products. Thus, the processing element 405 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 405 may be configured for a particular use or configured to execute instructions stored in volatile or non-volatile media or otherwise accessible to the processing element 405. As such, whether configured by hardware or computer program products, or by a combination thereof, the processing element 405 may be capable of performing steps or operations according to embodiments of the present invention when configured accordingly.

In one embodiment, the heightened need prediction computing entity 106 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 410, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. As will be recognized, the non-volatile storage or memory media may store datasets, dataset instances, dataset management systems, data, applications, programs, program modules, scripts, source code, object code, byte code, compiled code, interpreted code, machine code, executable instructions, and/or the like. The term dataset, dataset instance, dataset management system, and/or similar terms used herein interchangeably may refer to a collection of records or data that is stored in a computer-readable storage medium using one or more dataset models, such as a hierarchical dataset model, network model, relational model, entity-relationship model, object model, document model, semantic model, graph model, and/or the like.

In one embodiment, the heightened need prediction computing entity 106 may further include or be in communication with volatile media (also referred to as volatile storage, memory, memory storage, memory circuitry and/or similar terms used herein interchangeably). In one embodiment, the volatile storage or memory may also include one or more volatile storage or memory media 415, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. As will be recognized, the volatile storage or memory media may be used to store at least portions of the datasets, dataset instances, dataset management systems, data, applications, programs, program modules, scripts, source code, object code, byte code, compiled code, interpreted code, machine code, executable instructions, and/or the like being executed by, for example, the processing element 405. Thus, the datasets, dataset instances, dataset management systems, data, applications, programs, program modules, scripts, source code, object code, byte code, compiled code, interpreted code, machine code, executable instructions, and/or the like may be used to control certain aspects of the operation of the heightened need prediction computing entity 106 with the assistance of the processing element 405 and operating system.

As indicated, in one embodiment, the heightened need prediction computing entity 106 may also include one or more communications interfaces 420 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the heightened need prediction computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the heightened need prediction computing entity 106 may include or be in communication with one or more input elements, such as a keyboard input, a mouse input, a touch screen/display input, motion input, movement input, audio input, pointing device input, joystick input, keypad input, and/or the like. The sensor computing entity 105 may also include or be in communication with one or more output elements (not shown), such as audio output, video output, screen/display output, motion output, movement output, and/or the like.

V. EXEMPLARY SYSTEM OPERATIONS

Various embodiments of the present invention disclose techniques for reliably and efficiently performing user condition monitoring (e.g., heightened need prediction) that creatively utilize machine learning models to reduce the computational complexity and the storage complexity of performing such user condition monitoring actions. The machine learning techniques used herein to perform user condition monitoring are designed to have an asymmetric cost profile, a property that causes much of the costs of user condition monitoring performed using the noted machine learning models to be shifted to training time, which in turn reduces the amount of computations and/or the amount of model-definition data needed to perform effective and reliable user condition monitoring post-training.

Passive Heightened Need Prediction

FIG. 5 is a flowchart diagram of an example process 500 for performing passive heightened need prediction for a user profile. Via the various steps/operations of the process 500, the heightened need prediction computing entity 106 can utilize incoming monitoring data provided by the sensor computing entities 105 and the client computing entities 102 to effectively and efficiently detect heightened need conditions associated with the user profile as well as to cause client computing entities 102 to perform responsive actions in response to the detected heightened need conditions.

The process 500 includes a loop that in turn comprises steps/operations 501-504. The steps/operations 501-504 may be executed during an online prediction phase for the heightened need prediction computing entity 106. The online prediction phase may be a data object that describes configuration parameters for operation of the heightened need prediction computing entity 106 during a period in which the heightened need prediction computing entity 106 is configured to determine one or more heightened need predictions for a user profile based on incoming monitoring data associated with the user profile and by using a trained heightened need prediction machine learning model. In some embodiments, the time period described by the online prediction phase may be preceded by a time period described by an offline training phase. In the noted embodiments, the offline training phase may be a data object that describes configuration parameters for the operation of the heightened need prediction computing entity 106 during a time period prior to the time period described by the online prediction phase in which the heightened need prediction computing entity 106 is configured to generate the trained heightened need prediction machine learning model based on training monitoring data associated with the user profile. In some embodiments, the time period described by the online prediction phase may also comprise generating or updating the trained heightened need prediction machine learning model based on incoming training monitoring data associated with the user profile.

The loop corresponding to the process 500 may begin at step/operation 501 when the heightened need prediction computing entity 106 receives incoming monitoring data associated with the user profile from the sensor computing entities 105. The incoming monitoring data may include a collection of one or more data objects that describe information about one or more recorded conditions and/or one or more recorded activities of an end user associated with the user profile during a current time interval of the online prediction phase. For example, the incoming monitoring data may include one or more data objects that describe one or more recorded physiological conditions (e.g., a blood pressure, a heart rate, an electrocardiogram, a breathing rate, an acceleration rate, a galvanic skin response, a body temperature, a beating rate, an electromyogram, an electroencephalogram, a blood oxygen, and/or the like) of the end user associated with the user profile during the current time interval of the online prediction phase. As another example, the incoming monitoring data may include one or more data objects that describe one or more behavioral conditions (e.g., one or more arm movements, one or more eye movement patterns, an eye blinking rate, a bone reflex speed, and/or the like) of the end user associated with the user profile during the current time interval of the online prediction phase. As yet another example, the incoming monitoring data may include one or more location markers for the end user associated with the user profile during the current time interval of the online prediction phase. As a further example, the incoming monitoring data may include one or more data objects that describe one or more facial features of the end user associated with the user profile during the current time interval of the online prediction phase.

In some embodiments, the heightened need prediction computing entity 106 receives the incoming monitoring data from sensor devices associated with the sensor computing entities 105. For example, the heightened need prediction computing entity 106 may receive a portion of the incoming monitoring data from sensor devices associated with a smartphone device. Examples of incoming monitoring data that may be obtained from smartphone device sensors may include accelerometer data, location data, facial feature data, eye movement data, heart rate data, and/or the like. As another example, the heightened need prediction computing entity 106 may receive a portion of the incoming monitoring data from medical sensor devices connected to various locations within the physiological anatomy of the end user associated with the user profile. Examples of the noted medical sensor devices include chest straps, heart-rate detectors, insulin-level detectors, blood pressure detectors, and/or the like. As yet another example, the heightened need prediction computing entity 106 may receive a portion of the incoming monitoring data from medical sensor devices associated with a smart watch device. As a further example, the heightened need prediction computing entity 106 may receive a portion of the incoming monitoring data from medical sensor devices associated with a personal assistant device (e.g., Alexa, Siri, Google Home, a virtual-reality-enabled personal assistant device, and/or the like).

An operational example of a monitoring data object 900 that may include incoming monitoring data is depicted in FIG. 9. The monitoring data object 900 includes physiological data associated with seven physiological sensors. As depicted in FIG. 9, each physiological sensor of the seven physiological sensors is associated with a monitoring data signal that depicts the recorded values of the physiological sensor over a period of time described by the horizontal axis of the monitoring data object 900. For example, as depicted in FIG. 9, the physiological sensor 901 (which is a heart-rate-detecting sensor) is associated with the monitoring data signal 911. The monitoring data object 900 further depicts monitoring windows (described below) using dotted lines that divide the horizontal range of the monitoring data object 900 into various subranges (i.e., various temporal subranges). Thus, as depicted in FIG. 9, the monitoring data object 900 depicts monitoring windows 921-926.

Returning to FIG. 5, at step/operation 502, the heightened need prediction computing entity 106 processes the incoming monitoring data using a trained heightened need prediction machine learning model to determine a heightened need prediction for a current incoming monitoring window of the incoming monitoring data. The incoming monitoring window may be a data object that describes a subset of the incoming monitoring data that is deemed to be temporally adequate (e.g., lengthy enough) to use in order to determine whether the end user associated with the user profile is experiencing a heightened need condition. For example, configuration data for the heightened need prediction computing entity 106 may require that the incoming monitoring data be divided into disjoint subsets each associated with a predefined length of time (e.g., five seconds of time), and that each disjoint subset be deemed an incoming monitoring window. As another example, configuration data for the heightened need prediction computing entity 106 may require that the incoming monitoring data be divided into disjoint subsets each defined based on proximity to a detected user action (e.g., to a detected deep-breathing action), and that each disjoint subset be deemed an incoming monitoring window. In some embodiments, to determine the incoming monitoring window, the heightened need prediction computing entity 106 performs anomaly reduction on the incoming monitoring data to generate anomaly-reduced incoming monitoring data and determines the incoming monitoring window based on the anomaly-reduced incoming monitoring data.

The heightened need prediction may be a data object that describes an estimated determination about whether a corresponding incoming monitoring window describes a period of time in which need for a target activity and/or a target substance by the end user associated with the user profile is beyond an ordinary level of need for the target activity and/or the target substance. Examples of heightened need conditions that characterize heightened need periods include craving conditions, such as cravings for nicotine, for sugar, for particular addictive behaviors, and/or the like. In some embodiments, to determine the heightened need prediction for a corresponding incoming monitoring window, the heightened need prediction computing entity 106 processes the incoming monitoring window using a trained heightened need prediction machine learning model to determine the heightened need prediction for the incoming monitoring window.

An operational example of a heightened need prediction data object 1000 that can be used to describe heightened need predictions for the monitoring windows 921-926 depicted in the monitoring data object 900 of FIG. 9. As depicted in FIG. 10, a monitoring window 921-926 is deemed to have a positive heightened need prediction if it intersects with a heightened-need condition 1001-1003 and is deemed to have a negative heightened need prediction if it does not intersect with a heightened-need condition 1001-1003. Accordingly, as depicted in FIG. 9, the monitoring window 921 is deemed to have a negative heightened need prediction because it does not intersect with a heightened-need condition, the monitoring window 922 is deemed to have a positive heightened need prediction because it intersects with the heightened need condition 1001, the monitoring window 923 is deemed to have a positive heightened need prediction because it intersects with the heightened need condition 1001 and the heightened need condition 1002, the monitoring window 924 is deemed to have a positive heightened need prediction because it intersects with the heightened need condition 1002, the monitoring window 925 is deemed to have a positive heightened need prediction because it intersects with the heightened need condition 1003, the monitoring window 926 is deemed to have a positive heightened need prediction because it intersects with the heightened need condition 1003, and the monitoring window 921 is deemed to have a negative heightened need prediction because it does not intersect with a heightened-need condition.

In some embodiments, the heightened need prediction computing entity 106 determines that the heightened need prediction for the incoming monitoring window is positive if the heightened need prediction computing entity 106 determines that the heightened need prediction for the incoming monitoring window describes that the incoming monitoring window is predicted to include a heightened need period. In some embodiments, the heightened need prediction computing entity 106 determines that the heightened need prediction for the incoming monitoring window is negative if the heightened need prediction computing entity 106 determines that the heightened need prediction for the incoming monitoring window does not describe that the incoming monitoring window is predicted to include a heightened need period.

Returning to FIG. 5, at step/operation 503, in response to determining that the heightened need prediction for the incoming monitoring window is positive, the heightened need prediction computing entity 106 performs one or more responsive actions by communicating with the client computing entities 102 associated with the user profile. In some embodiments, the heightened need prediction computing entity 106 performs one or more responsive actions by causing the client computing entities 102 to display one or more user interfaces and/or enable one or more user functionalities. For example, as depicted in the responsive action user interface 1200 of FIG. 12, the heightened need prediction computing entity 106 has caused a client computing entity 102 to generate a user interface that enables the end-user to record a voice recording based on a displayed text during the duration of a detected heightened-need period (e.g., a craving period for smoking).

In some embodiments, to perform the one or more responsive actions, the heightened need prediction computing entity 106 determines an optimal need-reducing action for the user profile and communicates the optimal need-reducing action to at least one of the client computing entities 102 associated with the user profile. For example, the heightened need prediction computing entity 106 may communicate the optimal need-reducing action to a smartphone device associated with the user profile. As another example, the heightened need prediction computing entity 106 may communicate the optimal need-reducing action to a music player device associated with the user profile. As yet another example, the heightened need prediction computing entity 106 may communicate the optimal need-reducing action to a haptic signal device that is configured to be connected to be a particular location within the physiological anatomy of the end user associated with the user profile. As a further example, the heightened need prediction computing entity 106 may communicate the optimal need-reducing action to a smartwatch device associated with the user profile.

The optimal need-reducing action may be a data object that describes a real-world action configured to be performed by the end user associated with the user profile, where the real-world action is configured to be most adapted to lessen a predicted level of need for a target activity and/or a target substance by the end user. The optimal need-reducing action may be selected from a list of candidate need-reducing actions based on at least one of subject matter domain data, configuration data associated with a client computing entity for the user profile, historical data about past efficacy of responsive actions performed by the user profile in reducing need levels during heightened need periods, and/or the like. In some embodiments, to determine the optimal need-reducing action for the user profile, the heightened need prediction computing entity 106 utilizes an optimal action determination model, such as a trained optimal action determination model.

In some embodiments, the optimal action determination model is configured to determine, for each candidate need-reducing action of one or more candidate need-reducing actions, a need reduction likelihood value based on one or more trained parameters of the optimal action determination model. In some embodiments, the optimal action determination model is configured to determine, for each candidate need-reducing action of one or more candidate need-reducing actions, a need reduction speed value based on one or more trained parameters of the optimal action determination model. In some embodiments, the optimal action determination model is configured to determine, for each candidate need-reducing action of one or more candidate need-reducing actions, a need reduction likelihood value and a need reduction speed value based on one or more trained parameters of the optimal action determination model.

In some embodiments, the trained parameters of the optimal action determination model may define a generalized linear model that is configured to receive as inputs at least one of the following: (i) one or more input variables describing past behavioral patterns of a target end user in relation to different candidate need-reducing actions, (ii) one or more input variables describing past behaviors of a community of end users addicted to a target need-inducing activity and/or a target need-inducing substance (e.g., a target addictive activity and/or a target addictive substance) in relation to different candidate need-reducing actions, (iii) one or more technological capabilities of the target end user in relation to different candidate need-reducing actions (e.g., whether a smartphone device of the target end user enables particular need-reducing actions), (iv) one or more environmental conditions/constraints of the target end user in relation to different candidate need-reducing actions, and (iv) one or more time conditions/constraints of the target end user in relation to different candidate need-reducing actions.

In some embodiments, the optimal action determination model may define an optimal need-reducing action for each heightened need condition and/or for each monitoring window having a positive heightened-need condition. For example, as depicted in the optimal action determination data object 1100 of FIG. 11, each of the heightened need conditions 1001-1003 depicted in the heightened need prediction data object 1000 of FIG. 10 is associated with a corresponding optimal need-reducing action. In particular, as depicted in FIG. 11, the heightened need condition 1001 is associated with the optimal need-reducing action 1101, the heightened need condition 1002 is associated with the optimal need-reducing action 1102, and the heightened need condition 1003 is associated with the optimal need-reducing action 1103.

At step/operation 504, the heightened need prediction computing entity 106 monitors post-response incoming monitoring data until the heightened need prediction computing entity 106 detects a post-response incoming monitoring window having a negative heightened need prediction. In some embodiments, subsequent to performing the responsive actions at step/operation 503, the heightened need prediction computing entity 106 performs one or more post-response user monitoring iterations until the heightened need prediction computing entity 106 detects a post-response heightened need prediction that is negative (e.g., a post-response heightened need prediction that describes that a corresponding incoming monitoring window is predicted to describe an ordinary need period).

In some of the embodiments noted in the preceding paragraph, performing each current post-response user monitoring iteration of the one or more post-response user monitoring iterations includes: (i) determining a post-response incoming monitoring window for the current post-response user monitoring iteration (e.g., based on a current portion of the post-response incoming monitoring data that is associated with a time interval immediately subsequent to the time interval of a preceding portion of the post-response incoming monitoring data that is associated with a preceding post-response user monitoring iteration of the one or more post-response user monitoring iterations), and (ii) processing the post-responsive incoming monitoring window for the current post-response user monitoring iteration using the heightened need prediction machine learning model to generate a post-response heightened need prediction for the current post-response user monitoring iteration.

The post-response incoming monitoring data may be incoming monitoring data associated with a time interval that occurs subsequent to performing responsive actions in response to detecting a positive heightened need prediction. For example, the post-response incoming monitoring data may be associated with a time interval that occurs immediately after performing responsive actions in response to detecting a positive heightened need prediction. As another example, the post-response incoming monitoring data may be associated with a time interval that occurs immediately after the passage of an expected reactive latency period after performing responsive actions in response to detecting a positive heightened need prediction, where the expected reactive latency period may include an expected time interval required for performing the optimal need-reducing action associated with the responsive actions.

The post-response incoming monitoring window may be a data object that describes a subset of the post-response incoming monitoring data that is deemed to be temporally adequate (e.g., lengthy enough) to use in order to determine whether the end user associated with the user profile is experiencing a heightened need condition. For example, configuration data for the heightened need prediction computing entity 106 may require that the post-response incoming monitoring data be divided into disjoint subsets each associated with a predefined length of time (e.g., five seconds of time), and that each disjoint subset be deemed a post-response incoming monitoring window. As another example, configuration data for the heightened need prediction computing entity 106 may require that the post-response incoming monitoring data be divided into disjoint subsets each defined based on proximity to a detected user action (e.g., to a detected deep-breathing action), and that each disjoint subset be deemed a post-response incoming monitoring window. In some embodiments, to determine a post-response incoming monitoring window, the heightened need prediction computing entity 106 performs anomaly reduction on the post-response incoming monitoring data to generate anomaly-reduced post-response incoming monitoring data and determines the post-response incoming monitoring window based on the anomaly-reduced post-response incoming monitoring data.

In some embodiments, subsequent to performing the step/operation 503, the heightened need prediction computing entity 106 may use data about success of the recommended need-reducing actions to updating the parameters of the trained optimal action determination model. For example, in some embodiments, the parameter for each candidate need-reducing action may be determined based on an success ratio for the candidate need-reducing action, where the success ratio for a particular candidate need-reducing action is the ratio of the number of times that the particular candidate need-reducing action has succeeded in substantially reducing heightened need within a threshold period to the number of times that the need-reducing action has been recommended by the heightened need prediction computing entity 106 as an optimal need-reducing action. In some of the noted embodiments, upon detecting success/failure of a particular optimal need-reducing action in substantially reducing heightened need within a threshold period, the heightened need prediction computing entity 106 may update the success ratio of the noted optimal need-reducing ratio based on the noted success/failure of the particular need-reducing action and subsequently update the parameter of the noted optimal need-reducing ratio based on the updated success ratio for the noted optimal need-reducing ratio.

The loop corresponding to the process 500 continues back to step/operation 501 when, at step/operation 504, the heightened need prediction computing entity 106 determines a negative heightened need prediction for a post-responsive incoming monitoring window. By looping back to step/operation 501, the heightened need prediction computing entity 106 enables continuous monitoring of both heightened need scenarios and need-reduction scenarios following the heightened need scenarios. Of course, as discussed above, both continuous monitoring tasks rely on a trained heightened need prediction machine learning model. Example techniques for generating and/or updating such a trained heightened need prediction machine learning model are described in greater detail below, for example with reference to FIGS. 6-8.

Offline Training of Heightened Need Prediction Machine Learning Models

FIG. 6 provides a flowchart diagram of an example process 600 for performing passive heightened need prediction for a user profile using an offline-trained heightened need prediction machine learning model. The offline-trained heightened need prediction machine learning model is a heightened need prediction machine learning model that is exclusively trained during the offline training phase. The process 600 includes an offline training sub-process 601 that is performed during the offline training phase as well as an online prediction sub-process 602 that is performed during the online prediction phase.

The offline training sub-process 601 begins at step/operation 611 when the heightened need prediction computing entity 106 receives preexisting training monitoring data associated with the user profile. The preexisting training monitoring data may include a collection of one or more data objects that describe information about one or more recorded conditions and/or one or more recorded activities of an end user associated with the user profile during a past time interval associated with the offline training phase, where the collection of one or more data objects are associated with one or more heightened need ground-truths. For example, the preexisting training monitoring data may include one or more data objects that describe one or more recorded physiological conditions (e.g., a blood pressure, a heart rate, an electrocardiogram, a breathing rate, an acceleration rate, a galvanic skin response, a body temperature, a beating rate, an electromyogram, an electroencephalogram, a blood oxygen, and/or the like) of the end user associated with the user profile during the past time interval associated with the offline training phase. As another example, the preexisting training monitoring data may include one or more data objects that describe one or more behavioral conditions (e.g., one or more arm movements, one or more eye movement patterns, an eye blinking rate, a bone reflex speed, and/or the like) of the end user associated with the user profile during the past time interval associated with the offline training phase. As yet another example, the preexisting training monitoring data may include one or more location markers for the end user associated with the user profile during the current time interval of the online prediction phase. As a further example, the incoming monitoring data may include one or more data objects that describe one or more facial features of the end user associated with the user profile during the past time interval associated with the offline training phase.

At step/operation 612, the heightened need prediction computing entity 106 performs anomaly reduction on the preexisting training monitoring data to generate anomaly-reduced preexisting training monitoring data. In some embodiments, to perform anomaly reduction on the preexisting training monitoring data, the heightened need prediction computing entity 106 removes outlier values from the preexisting training monitoring data in order to generate anomaly-reduced preexisting training monitoring data. In some embodiments, to perform anomaly reduction on the preexisting training monitoring data, the heightened need prediction computing entity 106 removes noise values from the preexisting training monitoring data in order to generate anomaly-reduced preexisting training monitoring data. In some embodiments, to perform anomaly reduction on the preexisting training monitoring data, the heightened need prediction computing entity 106 removes mis-recorded values from the preexisting training monitoring data in order to generate anomaly-reduced preexisting training monitoring data. In some embodiments, to perform anomaly reduction on the preexisting training monitoring data, the heightened need prediction computing entity 106 removes values within the preexisting training monitoring data that are estimated to be mis-recorded based on a distribution of the preexisting training monitoring data from the preexisting training monitoring data in order to generate anomaly-reduced preexisting training monitoring data.

At step/operation 613, the heightened need prediction computing entity 106 generates one or more preexisting training monitoring windows based on the anomaly-reduced preexisting training monitoring data. A preexisting training monitoring window may be a data object that describes a subset of the preexisting training monitoring data that is deemed to be temporally adequate (e.g., lengthy enough) to use in order to generate the heightened need prediction machine learning model during the offline training phase based on a deviation measure between an inferred heightened need prediction for the preexisting training monitoring window and a heightened need ground-truth for the preexisting training monitoring window. For example, configuration data for the heightened need prediction computing entity 106 may require that a batch of preexisting training monitoring data be divided into disjoint or overlapping subsets each associated with a predefined length of time (e.g., five seconds of time), and that each disjoint subset be deemed a preexisting training monitoring window. As another example, configuration data for the heightened need prediction computing entity 106 may require that a batch of the incoming monitoring data be divided into disjoint subsets each defined based on proximity to a detected user action (e.g., to a detected deep-breathing action), and that each disjoint subset be deemed a preexisting training monitoring window.

In some embodiments, the heightened need prediction computing entity 106 processes each preexisting training monitoring window using an untrained heightened need prediction machine learning model to determine an offline-inferred heightened need prediction for the training monitoring window. An offline-inferred heightened need prediction may be a data object that describes a heightened need prediction for a corresponding preexisting training monitoring window, where the noted heightened need prediction is determined as part of the process of training/updating a heightened need prediction machine learning model during the offline training stage for the heightened need prediction machine learning model. In other words, the offline-inferred heightened need prediction is a data object that describes a heightened need prediction generated during the process of training/updating a heightened need prediction machine learning model during the offline training stage for the heightened need prediction machine learning model.

At step/operation 614, the heightened need prediction computing entity 106 identifies an offline-inferred heightened need ground-truth for each preexisting training monitoring window. The offline-inferred heightened need ground-truth may be a data object that describes information about whether a corresponding preexisting training monitoring window describes a heightened need condition based on real-world data describing end user intentions and/or end user actions during the time interval associated with the corresponding preexisting training monitoring window. For example, the offline-inferred heightened need ground-truth may be determined based on direct user input describing that the user is experiencing a craving condition at a time associated with inputting the direct user input. As another example, the offline-inferred heightened need ground-truth may describe that a target end user is engaging in a need response action at a time associated with the corresponding preexisting training monitoring window for the offline-inferred heightened need ground-truth, where the need response action may be a data object that describes an action expected to be performed in response to a heightened need condition, such as a cigarette smoking action.

In some embodiments, the heightened need prediction computing entity 106 may be configured to detect (e.g., based on arm movements of an end user, based on signals provided by a smart electrical lighter, and/or the like) that an end user has likely engaged in smoking cigarette, and use the noted detection to determine that a preexisting training monitoring window associated with the action detection time, an estimated action performance time, and/or an estimated action craving time has a positive offline-inferred heighted need ground-truth. In some of the noted embodiments, an estimated craving time may be determined to be within a temporal range comprising n time units before and m time units after the action detection time, where the values of n and m may be determined based on one or more psychological attributes of the end-user and/or one or more past behavioral patterns of the end-user.

At step/operation 615, the heightened need prediction computing entity 106 generates the trained heightened need prediction machine learning model based on each the offline-inferred heightened need ground-truth for the preexisting training monitoring window. In some of the noted embodiments, the heightened need prediction computing entity 106 calculates an error function for the trained heightened need prediction machine learning model based on each measure of deviation for a preexisting training time window, where the measure of deviation of a preexisting training time window is determined based on a difference between the offline-inferred heightened need prediction for the preexisting training time window and the offline-inferred heightened need ground-truth for preexisting training time window. In some of the noted embodiments, the heightened need prediction computing entity 106 generates the trained heightened need prediction machine learning model by setting the parameters of the trained heightened need prediction machine learning model in order to minimize the error function.

As depicted in FIG. 6, after performing the offline training sub-process 601 during the offline training stage, the online prediction sub-process 602 during the online prediction stage is performed. The online prediction sub-process 602 begins at step/operation 621 when the heightened need prediction computing entity 106 retrieves incoming monitoring data associated with the user profile. Retrieving the monitoring data is discussed in greater detail above with reference to step/operation 501 of process 500 of FIG. 5.

At step/operation 622, the heightened need prediction computing entity 106 performs anomaly reduction on the incoming monitoring data to generate anomaly-reduced incoming monitoring data. In some embodiments, to perform anomaly reduction on the incoming monitoring data, the heightened need prediction computing entity 106 removes outlier values from the incoming monitoring data in order to generate anomaly-reduced incoming monitoring data. In some embodiments, to perform anomaly reduction on the incoming monitoring data, the heightened need prediction computing entity 106 removes noise values from the incoming monitoring data in order to generate anomaly-reduced incoming monitoring data. In some embodiments, to perform anomaly reduction on the incoming monitoring data, the heightened need prediction computing entity 106 removes mis-recorded values from the incoming monitoring data in order to generate anomaly-reduced incoming monitoring data. In some embodiments, to perform anomaly reduction on the incoming monitoring data, the heightened need prediction computing entity 106 removes values within the incoming monitoring data that are estimated to be mis-recorded based on a distribution of the incoming monitoring data from the incoming monitoring data in order to generate anomaly-reduced incoming monitoring data.

At step/operation 623, the heightened need prediction computing entity 106 generates an incoming monitoring window based on the anomaly-reduced incoming monitoring data. Generating the incoming monitoring windows based on incoming monitoring data is described in greater detail below with reference to step/operation 502 of process 500 of FIG. 5. The same techniques can be utilized to generate incoming monitoring windows based on anomaly-reduced incoming monitoring data.

At step/operation 624, the heightened need prediction computing entity 106 processes the incoming monitoring window using the trained heightened need prediction machine learning model generated using the offline training sub-process 601 to generate a heightened need prediction for the incoming monitoring window. Generating heightened need predictions for incoming monitoring windows is described in greater detail below with reference to the step/operation 502 of process 500 of FIG. 5.

At step/operation 625, in response to determining that the heightened need prediction is positive, the heightened need prediction computing entity 106 performs one or more responsive actions by communicating with one or more client computing entities 102 associated with the user profile. Performing responsive actions is described in greater detail below with reference to the step/operation 503 of process 500 of FIG. 5.

Online Training of Heightened Need Prediction Machine Learning Models

FIG. 7 provides a flowchart diagram of an example process 700 for performing passive heightened need prediction for a user profile using an online-trained heightened need prediction machine learning model. The online-trained heightened need prediction machine learning model is a heightened need prediction machine learning model that is exclusively trained during the online prediction phase. The process 700 starts includes an online prediction/training sub-process 701 that is performed during the online prediction phase.

The online prediction/training sub-process 701 begins at step/operation 711 when the heightened need prediction computing entity 106 identifies an incoming monitoring window. In some embodiments, to identify an incoming monitoring window, the heightened need prediction computing entity 106 retrieves incoming monitoring data, performs anomaly reduction on the incoming monitoring data to generate anomaly-reduced incoming monitoring data, and generates an incoming monitoring window based on the anomaly-reduced incoming monitoring data.

At step/operation 712, the heightened need prediction computing entity 106 determines whether the incoming monitoring window is associated with an online-inferred heightened need ground-truth. The online-inferred heightened need ground-truth may be a data object that describes information about whether a corresponding incoming monitoring window describes a heightened need condition based on real-world data describing end user intentions and/or end user actions during the time interval associated with the corresponding preexisting training monitoring window, where the real-world data are obtained during the online prediction stage for a corresponding heightened need prediction machine learning model.

In some embodiments, there may be a delay between obtaining an incoming monitoring window and obtaining an online-inferred heightened need ground-truth for the noted incoming monitoring window. For example, biometric data windows may be received in real-time, while ground-truth craving identifications for the noted biometric data windows may be received with a few minutes of delay. In some of the noted embodiments, at prediction time, the heightened need prediction computing entity 106 may perform the step/operation 712 in accordance with the lack of receipt of the online-inferred heightened need ground-truth to determine that the incoming monitoring window is not associated with the online-inferred heightened need ground-truth, which in turn leads the heightened need prediction computing entity 106 to select to perform step/operation 713 instead of step/operation 715. However, in response to receiving the online-inferred heightened need ground-truth at a time subsequent to the prediction time, the heightened need prediction computing entity 106 may perform step/operation 714 to update the trained heightened need prediction machine learning model based on the received online-inferred heightened need ground-truth.

For example, the online-inferred heightened need ground-truth may be determined based on direct user input describing that the user is experiencing a craving condition at a time associated with inputting the direct user input. As another example, the online-inferred heightened need ground-truth may describe that a target end user is engaging in a need response action at a time associated with the corresponding incoming monitoring window for the online-inferred heightened need ground-truth, where the need response action may be a data object that describes an action expected to be performed in response to a heightened need condition, such as a cigarette smoking action.

As depicted in FIG. 7, in response to determining that the incoming monitoring window is not associated with an online-inferred heightened need ground-truth, the heightened need prediction computing entity 106 proceeds to step/operation 713 to process the incoming monitoring window using the trained heightened need prediction machine learning model to generate the heightened need prediction for the incoming monitoring window. Thus, in response to determining that the incoming monitoring window is not associated with an online-inferred heightened need ground-truth, no training/updating of the heightened need detection machine learning model is performed and the existing version of the model is utilized to generate the heightened need prediction for the incoming monitoring window.

However, in response to determining that the incoming monitoring window is associated with an online-inferred heightened need ground-truth, the heightened need prediction computing entity 106 proceeds to step/operation 714 to update one or more parameters of the trained heightened need prediction machine learning model based on a deviation measure between an online-inferred heightened need prediction for the incoming monitoring window and the online-inferred heightened need ground-truth for the incoming monitoring window. An online-inferred heightened need prediction may be a data object that describes a heightened need prediction for a corresponding incoming monitoring window that is generated using a trained heightened need prediction machine learning model prior to updating/retraining of the trained heightened need prediction machine learning model based on a deviation measure between the online-inferred heightened need prediction for the incoming monitoring window and the online-inferred heightened need ground-truth for the incoming monitoring window. Afterward, at step/operation 715, the heightened need prediction computing entity 106 utilizes the updated trained heightened need prediction machine learning model to generate the heightened need prediction for the incoming monitoring window.

At step/operation 716, the heightened need prediction computing entity 106 performs one or more prediction-based actions based on the heightened need prediction for the incoming monitoring window. Performing responsive actions is described in greater detail below with reference to the step/operation 503 of process 500 of FIG. 5.

Hybrid Training of Heightened Need Prediction Machine Learning Models

FIG. 8 is a flowchart diagram of an example process 800 for performing passive heightened need prediction for a user profile using a hybrid-trained heightened need prediction machine learning model. The hybrid-trained heightened need prediction machine learning model is a heightened need prediction machine learning model that is trained both during the offline training phase and the online prediction phase. The process 800 includes an offline training sub-process 801 that is performed during the offline training phase as well as an online prediction/training sub-process 802 that is performed during the online prediction phase.

The offline training sub-process 801 begins at step/operation 811 when the heightened need prediction computing entity 106 receives preexisting training monitoring data associated with the user profile. The preexisting training monitoring data may include a collection of one or more data objects that describe information about one or more recorded conditions and/or one or more recorded activities of an end user associated with the user profile during a past time interval associated with the offline training phase, where the collection of one or more data objects are associated with one or more heightened need ground-truths. For example, the preexisting training monitoring data may include one or more data objects that describe one or more recorded physiological conditions (e.g., a blood pressure, a heart rate, an electrocardiogram, a breathing rate, an acceleration rate, a galvanic skin response, a body temperature, a beating rate, an electromyogram, an electroencephalogram, a blood oxygen, and/or the like) of the end user associated with the user profile during the past time interval associated with the offline training phase. As another example, the preexisting training monitoring data may include one or more data objects that describe one or more behavioral conditions (e.g., one or more arm movements, one or more eye movement patterns, an eye blinking rate, a bone reflex speed, and/or the like) of the end user associated with the user profile during the past time interval associated with the offline training phase. As yet another example, the preexisting training monitoring data may include one or more location markers for the end user associated with the user profile during the current time interval of the online prediction phase. As a further example, the incoming monitoring data may include one or more data objects that describe one or more facial features of the end user associated with the user profile during the past time interval associated with the offline training phase.

At step/operation 812, the heightened need prediction computing entity 106 performs anomaly reduction on the preexisting training monitoring data to generate anomaly-reduced preexisting training monitoring data. In some embodiments, to perform anomaly reduction on the preexisting training monitoring data, the heightened need prediction computing entity 106 removes outlier values from the preexisting training monitoring data in order to generate anomaly-reduced preexisting training monitoring data. In some embodiments, to perform anomaly reduction on the preexisting training monitoring data, the heightened need prediction computing entity 106 removes noise values from the preexisting training monitoring data in order to generate anomaly-reduced preexisting training monitoring data. In some embodiments, to perform anomaly reduction on the preexisting training monitoring data, the heightened need prediction computing entity 106 removes mis-recorded values from the preexisting training monitoring data in order to generate anomaly-reduced preexisting training monitoring data. In some embodiments, to perform anomaly reduction on the preexisting training monitoring data, the heightened need prediction computing entity 106 removes values within the preexisting training monitoring data that are estimated to be mis-recorded based on a distribution of the preexisting training monitoring data from the preexisting training monitoring data in order to generate anomaly-reduced preexisting training monitoring data.

At step/operation 813, the heightened need prediction computing entity 106 generates one or more preexisting training monitoring windows based on the anomaly-reduced preexisting training monitoring data. A preexisting training monitoring window may be a data object that describes a subset of the preexisting training monitoring data that is deemed to be temporally adequate (e.g., lengthy enough) to use in order to generate the heightened need prediction machine learning model during the offline training phase based on a deviation measure between an inferred heightened need prediction for the preexisting training monitoring window and a heightened need ground-truth for the preexisting training monitoring window. For example, configuration data for the heightened need prediction computing entity 106 may require that a batch of preexisting training monitoring data be divided into disjoint subsets each associated with a predefined length of time (e.g., five seconds of time), and that each disjoint subset be deemed a preexisting training monitoring window. As another example, configuration data for the heightened need prediction computing entity 106 may require that a batch of the incoming monitoring data be divided into disjoint subsets each defined based on proximity to a detected user action (e.g., to a detected deep-breathing action), and that each disjoint subset be deemed a preexisting training monitoring window.

In some embodiments, the heightened need prediction computing entity 106 processes each preexisting training monitoring window using an untrained heightened need prediction machine learning model to determine an offline-inferred heightened need prediction for the training monitoring window. An offline-inferred heightened need prediction may be a data object that describes a heightened need prediction for a corresponding preexisting training monitoring window, where the noted heightened need prediction is determined as part of the process of training/updating a heightened need prediction machine learning model during the offline training stage for the heightened need prediction machine learning model. In other words, the offline-inferred heightened need prediction is a data object that describes a heightened need prediction generated during the process of training/updating a heightened need prediction machine learning model during the offline training stage for the heightened need prediction machine learning model.

At step/operation 814, the heightened need prediction computing entity 106 identifies an offline-inferred heightened need ground-truth for each preexisting training monitoring window. The offline-inferred heightened need ground-truth may be a data object that describes information about whether a corresponding preexisting training monitoring window describes a heightened need condition based on real-world data describing end user intentions and/or end user actions during the time interval associated with the corresponding preexisting training monitoring window. For example, the offline-inferred heightened need ground-truth may be determined based on direct user input describing that the user is experiencing a craving condition at a time associated with inputting the direct user input. As another example, the offline-inferred heightened need ground-truth may describe that a target end user is engaging in a need response action at a time associated with the corresponding preexisting training monitoring window for the offline-inferred heightened need ground-truth, where the need response action may be a data object that describes an action expected to be performed in response to a heightened need condition, such as a cigarette smoking action.

In some embodiments, the heightened need prediction computing entity 106 may be configured to detect (e.g., based on arm movements of an end user, based on signals provided by a smart electrical lighter, and/or the like) that an end user has likely engaged in smoking cigarette, and use the noted detection to classify a preexisting training monitoring window associated with the action detection time, an estimated action performance time, and/or an estimated action craving time as having a positive offline-inferred heightened need ground-truth. In some of the noted embodiments, an estimated craving time may be determined to be within n time units before the action detection time, where the value of n may be determined based on one or more psychological attributes and/or one or more past behavioral patterns of a corresponding user profile.

At step/operation 815, the heightened need prediction computing entity 106 generates the trained heightened need prediction machine learning model based on each the offline-inferred heightened need ground-truth for the preexisting training monitoring window. In some of the noted embodiments, the heightened need prediction computing entity 106 calculates an error function for the trained heightened need prediction machine learning model based on each measure of deviation for a preexisting training time window, where the measure of deviation of a preexisting training time window is determined based on a difference between the offline-inferred heightened need prediction for the preexisting training time window and the offline-inferred heightened need ground-truth for preexisting training time window. In some of the noted embodiments, the heightened need prediction computing entity 106 generates the trained heightened need prediction machine learning model by setting the parameters of the trained heightened need prediction machine learning model in order to minimize the error function.

As depicted in FIG. 8, after performing the offline training sub-process 801 during the offline training stage, the online prediction/training sub-process 802 during the online prediction stage is performed. The online prediction/training sub-process 802 begins at step/operation 821 when the heightened need prediction computing entity 106 identifies an incoming monitoring window. In some embodiments, to identify an incoming monitoring window, the heightened need prediction action computing entity 106 retrieves incoming monitoring data, performs anomaly reduction on the incoming monitoring data to generate anomaly-reduced incoming monitoring data, and generates an incoming monitoring window based on the anomaly-reduced incoming monitoring data.

At step/operation 822, the heightened need prediction computing entity 106 determines whether the incoming monitoring window is associated with an online-inferred heightened need ground-truth. The offline-inferred heightened need ground-truth may be a data object that describes information about whether a corresponding incoming monitoring window describes a heightened need condition based on real-world data describing end user intentions and/or end user actions during the time interval associated with the corresponding preexisting training monitoring window, where the real-world data are obtained during the online prediction stage for a corresponding heightened need prediction machine learning model. For example, the online-inferred heightened need ground-truth may be determined based on direct user input describing that the user is experiencing a craving condition at a time associated with inputting the direct user input. As another example, the online-inferred heightened need ground-truth may describe that a target end user is engaging in a need response action at a time associated with the corresponding incoming monitoring window for the online-inferred heightened need ground-truth, where the need response action may be a data object that describes an action expected to be performed in response to a heightened need condition, such as a cigarette smoking action.

In some embodiments, there may be a delay between obtaining an incoming monitoring window and obtaining an online-inferred heightened need ground-truth for the noted incoming monitoring window. For example, biometric data windows may be received in real-time, while ground-truth craving identifications for the noted biometric data windows may be received with a few minutes of delay. In some of the noted embodiments, at prediction time, the heightened need prediction computing entity 106 may perform the step/operation 822 in accordance with the lack of receipt of the online-inferred heightened need ground-truth to determine that the incoming monitoring window is not associated with the online-inferred heightened need ground-truth, which in turn leads the heightened need prediction computing entity 106 to select to perform step/operation 823 instead of step/operation 825. However, in response to receiving the online-inferred heightened need ground-truth at a time subsequent to the prediction time, the heightened need prediction computing entity 106 may perform step/operation 824 to update the trained heightened need prediction machine learning model based on the received online-inferred heightened need ground-truth.

As depicted in FIG. 8, in response to determining that the incoming monitoring window is not associated with an online-inferred heightened need ground-truth, the heightened need prediction computing entity 106 proceeds to step/operation 823 to process the incoming monitoring window using the trained heightened need prediction machine learning model to generate the heightened need prediction for the incoming monitoring window. Thus, in response to determining that the incoming monitoring window is not associated with an online-inferred heightened need ground-truth, no training/updating of the heightened need detection machine learning model is performed and the existing version of the model is utilized to generate the heightened need prediction for the incoming monitoring window.

However, in response to determining that the incoming monitoring window is associated with an online-inferred heightened need ground-truth, the heightened need prediction computing entity 106 proceeds to step/operation 824 to update one or more parameters of the trained heightened need prediction machine learning model based on a deviation measure between an online-inferred heightened need prediction for the incoming monitoring window and the online-inferred heightened need ground-truth for the incoming monitoring window. An online-inferred heightened need prediction may be a data object that describes a heightened need prediction for a corresponding incoming monitoring window that is generated using a trained heightened need prediction machine learning model prior to updating/retraining of the trained heightened need prediction machine learning model based on a deviation measure between the online-inferred heightened need prediction for the incoming monitoring window and the online-inferred heightened need ground-truth for the incoming monitoring window. Afterward, at step/operation 825, the heightened need prediction computing entity 106 utilizes the updated trained heightened need prediction machine learning model to generate the heightened need prediction for the incoming monitoring window.

At step/operation 826, the heightened need prediction computing entity 106 performs one or more prediction-based actions based on the heightened need prediction for the incoming monitoring window. Performing responsive actions is described in greater detail below with reference to the step/operation 503 of process 500 of FIG. 5.

VI. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method comprising:
  receiving, by one or more processors, incoming monitoring data associated with a user profile;
  generating, by the one or more processors, anomaly-reduced incoming monitoring data by removing values within the incoming monitoring data that are estimated to be mis-recorded based at least in part on a distribution of the incoming monitoring data;
  generating, by the one or more processors, an incoming monitoring window based at least in part on the anomaly-reduced incoming monitoring data, wherein the incoming monitoring window comprises a subset of the incoming monitoring data;
  accessing, by the one or more processors, a heightened need prediction machine learning model that is trained to determine heightened need prediction for an input incoming monitoring window based at least in part on a heightened need ground-truth that (i) comprises one or more heightened need conditions that are determined based at least in part on training monitoring data that is associated with the user profile and (ii) represents whether an end user associated with the user profile engaged in one or more need-response actions that are (a) associated with one or more target addictive activities or substances and (b) responsive to the one or more heightened need conditions;
  generating, by the one or more processors using the heightened need prediction machine learning model, a heightened need prediction for the incoming monitoring window, wherein the heightened need prediction indicates that the incoming monitoring window is associated with a need that is beyond a threshold level of need that is associated with the one or more target addictive activities or substances; and
  based at least in part on the heightened need prediction and using an optimal action determination machine learning model that is configured to generate one or more need reduction likelihood values or one or more need reduction speed values for one or more candidate need-reducing actions, initiating, by the one or more processors, performance of a responsive action from the one or more candidate need-reducing actions based at least in part on the one or more need reduction likelihood values or the one or more need reduction speed values, wherein the responsive action comprises communicating with one or more client devices associated with the user profile.

2. The computer-implemented method of claim 1, wherein the training monitoring data comprises preexisting training monitoring data and training the heightened need prediction machine learning model comprises:
  receiving the preexisting training monitoring data associated with the user profile;
  generating anomaly-reduced preexisting training monitoring data by performing anomaly reduction on the preexisting training monitoring data;
  generating one or more preexisting training monitoring windows based at least in part on the anomaly-reduced preexisting training monitoring data;
  for each preexisting training monitoring window of the one or more preexisting training monitoring windows:
    generating an offline-inferred heightened need prediction, and
    determining an offline-inferred heightened need ground-truth; and
  generating the heightened need prediction machine learning model based at least in part on the offline-inferred heightened need prediction and the offline-inferred heightened need ground-truth for each of the one or more preexisting training monitoring windows.

3. The computer-implemented method of claim 2, wherein the offline-inferred heightened need ground-truth is based at least in part on user monitoring data received from one or more user monitoring client devices associated with the user profile.

4. The computer-implemented method of claim 2, wherein the offline-inferred heightened need ground-truth represents whether a preexisting training monitoring window is associated with a given need-response action associated with the user profile.

5. The computer-implemented method of claim 1, wherein the training monitoring data comprises incoming training monitoring data and training the heightened need prediction machine learning model comprises:
   receiving the incoming training monitoring data associated with the user profile;
   generating anomaly-reduced incoming training monitoring data by performing anomaly reduction on the incoming training monitoring data;
   generating an incoming training monitoring window based at least in part on the anomaly-reduced incoming training monitoring data;
   generating an inferred heightened need prediction for the incoming training monitoring window;
   determining an incoming heightened need ground-truth for the incoming training monitoring window; and
   updating the heightened need prediction machine learning model based at least in part on the inferred heightened need prediction and the incoming heightened need ground-truth.

6. The computer-implemented method of claim 5, wherein the incoming heightened need ground-truth represents whether the incoming training monitoring window is associated with a given heightened need condition for the user profile.

7. The computer-implemented method of claim 1, wherein the training monitoring data comprises preexisting training monitoring data and incoming training monitoring data, and training the heightened need prediction machine learning model comprises:
   receiving the preexisting training monitoring data associated with the user profile;
   generating anomaly-reduced preexisting training monitoring data by performing anomaly reduction on the preexisting training monitoring data;
   generating one or more preexisting training monitoring windows based at least in part on the anomaly-reduced preexisting training monitoring data;
   for each preexisting training monitoring window of the one or more preexisting training monitoring windows:
      generating a preexisting inferred heightened need prediction, and
      determining a preexisting heightened need ground-truth;
   generating the heightened need prediction machine learning model based at least in part on the preexisting inferred heightened need prediction and the preexisting heightened need ground-truth;
   receiving the incoming training monitoring data associated with the user profile;
   generating anomaly-reduced incoming training monitoring data by performing anomaly reduction on the incoming training monitoring data;
   generating an incoming training monitoring window based at least in part on the anomaly-reduced incoming training monitoring data;
   generating an inferred heightened need prediction for the incoming training monitoring window;
   determining an incoming heightened need ground-truth for the incoming training monitoring window; and
   updating the heightened need prediction machine learning model based at least in part on the inferred heightened need prediction and the incoming heightened need ground-truth.

8. The computer-implemented method of claim 1, wherein initiating the performance of the responsive action comprises:
   determining, based at least in part on an optimal action determination model, an optimal need-reducing action for the user profile; and
   communicating the optimal need-reducing action to at least one of the one or more client devices.

9. A computing system comprising memory and one or more processors communicatively coupled to the memory, the one or more processors configured to:
   receive incoming monitoring data associated with a user profile;
   generate anomaly-reduced incoming monitoring data by removing values within the incoming monitoring data that are estimated to be mis-recorded based at least in part ona distribution of the incoming monitoring data;
   generate an incoming monitoring window based at least in part on the anomaly-reduced incoming monitoring data, wherein the incoming monitoring window comprises a subset of the incoming monitoring data;
   access a heightened need prediction machine learning model that is trained to determine heightened need prediction for an input incoming monitoring window based at least in part on a heightened need ground-truth that (i) comprises one or more heightened need conditions that are determined based at least in part on training monitoring data that is associated with the user profile and (ii) represents whether an end user associated with the user profile engaged in one or more need-response actions that are (a) associated with one or more target addictive activities or substances and (b) responsive to the one or more heightened need conditions;
   generate, using the heightened need prediction machine learning model, a heightened need prediction for the incoming monitoring window, wherein the heightened need prediction indicates that the incoming monitoring window is associated with a need that is beyond a threshold level of need that is associated with the one or more target addictive activities or substances; and
   based at least in part on the heightened need prediction and using an optimal action determination machine learning model that is configured to generate one or more need reduction likelihood values or one or more need reduction speed values for one or more candidate need-reducing actions, initiate performance of a responsive action, from the one or more candidate need-reducing actions based at least in part on the one or more need reduction likelihood values or the one or more need reduction speed values, wherein the responsive action comprises communicating with one or more client devices associated with the user profile.

10. The computing system of claim 9, wherein the training monitoring data comprises preexisting training monitoring data and the one or more processors are further configured to train the heightened need prediction machine learning model by:
   receiving the preexisting training monitoring data associated with the user profile;

generating anomaly-reduced preexisting training monitoring data by performing anomaly reduction on the preexisting training monitoring data;
generating one or more preexisting training monitoring windows based at least in part on the anomaly-reduced preexisting training monitoring data;
for each preexisting training monitoring window of the one or more preexisting training monitoring windows:
generating an offline-inferred heightened need prediction, and
determining an offline-inferred heightened need ground-truth; and
generating the heightened need prediction machine learning model based at least in part on the offline-inferred heightened need prediction and the offline-inferred heightened need ground-truth for each of the one or more preexisting training monitoring windows.

11. The computing system of claim 10, wherein the one or more processors are further configured to determine the offline-inferred heightened need ground-truth based at least in part on user monitoring data received from one or more user monitoring client devices associated with the user profile.

12. The computing system of claim 10, wherein the offline-inferred heightened need ground-truth represents whether a preexisting training monitoring window is associated with a given need-response action associated with the user profile.

13. The computing system of claim 9, wherein the training monitoring data comprises incoming training monitoring data and the one or more processors are further configured to train the heightened need prediction machine learning model is trained by:
receiving the incoming training monitoring data associated with the user profile;
generating anomaly-reduced incoming training monitoring data by performing anomaly reduction on the incoming training monitoring data;
generating an incoming training monitoring window based at least in part on the anomaly-reduced incoming training monitoring data;
generating an inferred heightened need prediction for the incoming training monitoring window;
determining an incoming heightened need ground-truth for the incoming training monitoring window; and
updating the heightened need prediction machine learning model based at least in part on the inferred heightened need prediction and the incoming heightened need ground-truth.

14. The computing system of claim 13, wherein the incoming heightened need ground-truth represents whether the incoming training monitoring window is associated with a given heightened need condition for the user profile.

15. The computing system of claim 9, wherein the training monitoring data comprises preexisting training monitoring data and incoming training monitoring data and the one or more processors are further configured to train the heightened need prediction machine learning model by:
receiving the preexisting training monitoring data associated with the user profile;
generating anomaly-reduced preexisting training monitoring data by performing anomaly reduction on the preexisting training monitoring data;
generating one or more preexisting training monitoring windows based at least in part on the anomaly-reduced preexisting training monitoring data;
for each preexisting training monitoring window of the one or more preexisting training monitoring windows:
generating a preexisting inferred heightened need prediction, and
determining a preexisting heightened need ground-truth;
generating the heightened need prediction machine learning model based at least in part on the preexisting inferred heightened need prediction and the preexisting heightened need ground-truth;
receiving the incoming training monitoring data associated with the user profile;
generating anomaly-reduced incoming training monitoring data by performing anomaly reduction on the incoming training monitoring data;
generating an incoming training monitoring window based at least in part on the anomaly-reduced incoming training monitoring data;
generating an inferred heightened need prediction for the incoming training monitoring window;
determining an incoming heightened need ground-truth for the incoming training monitoring window; and
updating the heightened need prediction machine learning model based at least in part on the inferred heightened need prediction and the incoming heightened need ground-truth.

16. The computing system of claim 9, wherein the one or more processors are further configured to initiate the performance of the responsive action by:
determining, based at least in part on an optimal action determination model, an optimal need-reducing action for the user profile; and
communicating the optimal need-reducing action to at least one of the one or more client devices.

17. One or more non-transitory computer-readable storage media including instructions that, that when executed by one or more processors, cause the one or more processors to:
receive incoming monitoring data associated with a user profile;
generate anomaly-reduced incoming monitoring data by removing values within the incoming monitoring data that are estimated to be mis-recorded based at least in part on a distribution of the incoming monitoring data;
generate an incoming monitoring window based at least in part on the anomaly-reduced incoming monitoring data, wherein the incoming monitoring window comprises a subset of the incoming monitoring data;
access a heightened need prediction machine learning model that is trained to determine heightened need prediction for an input incoming monitoring window based at least in part on a heightened need ground-truth that (i) comprises one or more heightened need conditions that are determined based at least in part on training monitoring data that is associated with the user profile and (ii) represents whether an end user associated with the user profile engaged in one or more need-response actions that are (a) associated with one or more target addictive activities or substances and (b) responsive to the one or more heightened need conditions;
generate, using the heightened need prediction machine learning model, a heightened need prediction for the incoming monitoring window, wherein the heightened need prediction indicates that the incoming monitoring window is associated with a need that is beyond a threshold level of need that is associated with the one or more target addictive activities or substances; and based at least in part on the heightened need prediction and using an optimal action determination machine learning model that is configured to generate one or more need reduction likelihood values or one or more need reduction speed values for one or more candidate need-reducing actions, initiate performance of a responsive action, from the one or more candidate need-reducing actions based at least in part on the one or more need reduction likelihood values or the one or more need reduction speed values, wherein the responsive action comprises communicating with one or more client devices associated with the user profile.

18. The one or more non-transitory computer-readable storage media of claim 17, wherein the training monitoring data comprises preexisting training monitoring data and further including instructions that, that when executed by the one or more processors, cause the one or more processors to train the heightened need prediction machine learning model by:

receiving the preexisting training monitoring data associated with the user profile;

generating anomaly-reduced preexisting training monitoring data by performing anomaly reduction on the preexisting training monitoring data;

generating one or more preexisting training monitoring windows based at least in part on the anomaly-reduced preexisting training monitoring data;

for each preexisting training monitoring window of the one or more preexisting training monitoring windows:

generating an offline-inferred heightened need prediction, and determining an offline-inferred heightened need ground-truth; and generating the heightened need prediction machine learning model based at least in part on the offline-inferred heightened need prediction and the offline-inferred heightened need ground-truth for each of the one or more preexisting training monitoring windows.

19. The one or more non-transitory computer-readable storage media of claim 17, wherein the training monitoring data comprises incoming training monitoring data and further including instructions that, that when executed by the one or more processors, cause the one or more processors to train the heightened need prediction machine learning model by:

receiving the incoming training monitoring data associated with the user profile;

generating anomaly-reduced incoming training monitoring data by performing anomaly reduction on the incoming training monitoring data;

generating an incoming training monitoring window based at least in part on the anomaly-reduced incoming training monitoring data;

generating an inferred heightened need prediction for the incoming training monitoring window;

determining an incoming heightened need ground-truth for the incoming training monitoring window; and updating the heightened need prediction machine learning model based at least in part on the inferred heightened need prediction and the incoming heightened need ground-truth.

20. The one or more non-transitory computer-readable storage media of claim 17, wherein the training monitoring data comprises preexisting training monitoring data and incoming training monitoring data and further including instructions that, that when executed by the one or more processors, cause the one or more processors to train the heightened need prediction machine learning model by:

receiving the preexisting training monitoring data associated with the user profile;

generating anomaly-reduced preexisting training monitoring data by performing anomaly reduction on the preexisting training monitoring data;

generating one or more preexisting training monitoring windows based at least in part on the anomaly-reduced preexisting training monitoring data;

for each preexisting training monitoring window of the one or more preexisting training monitoring windows:

generating a preexisting inferred heightened need prediction, and determining a preexisting heightened need ground-truth;

generating the heightened need prediction machine learning model based at least in part on the preexisting inferred heightened need prediction and the preexisting heightened need ground-truth;

receiving the incoming training monitoring data associated with the user profile;

generating anomaly-reduced incoming training monitoring data by performing anomaly reduction on the incoming training monitoring data;

generating an incoming training monitoring window based at least in part on the anomaly-reduced incoming training monitoring data;

generating an inferred heightened need prediction for the incoming training monitoring window;

determining an incoming heightened need ground-truth for the incoming training monitoring window; and updating the heightened need prediction machine learning model based at least in part on the inferred heightened need prediction and the incoming heightened need ground-truth.

\* \* \* \* \*

UNITED STATES PATENT AND TRADEMARK OFFICE
CERTIFICATE OF CORRECTION

| | | |
|---|---|---|
| PATENT NO. | : 12,236,320 B2 | Page 1 of 1 |
| APPLICATION NO. | : 16/866844 | |
| DATED | : February 25, 2025 | |
| INVENTOR(S) | : Peter Joseph Ross et al. | |

It is certified that error appears in the above-identified patent and that said Letters Patent is hereby corrected as shown below:

In the Claims

In Column 36, Line 24, Claim 9, delete "ona" and insert -- on a --, therefor.

Signed and Sealed this
Twentieth Day of May, 2025

Coke Morgan Stewart
*Acting Director of the United States Patent and Trademark Office*